United States Patent
Ray et al.

(10) Patent No.: US 9,332,998 B2
(45) Date of Patent: May 10, 2016

(54) APPARATUS AND METHODS FOR CLOT DISRUPTION AND EVACUATION

(71) Applicant: Covidien LP, Mansfield, MA (US)

(72) Inventors: Miranda Ray, San Jose, CA (US); Jessica Clayton, San Jose, CA (US); Lawrence Go, San Jose, CA (US); Michael Thai, San Jose, CA (US); James Hanlon, Morgan Hill, CA (US); Young Vo, San Jose, CA (US)

(73) Assignee: Covidien LP, Mansfield, MA (US)

( * ) Notice: Subject to any disclaimer, the term of this patent is extended or adjusted under 35 U.S.C. 154(b) by 291 days.

(21) Appl. No.: 13/835,324

(22) Filed: Mar. 15, 2013

(65) Prior Publication Data

US 2014/0046243 A1 Feb. 13, 2014

Related U.S. Application Data

(60) Provisional application No. 61/682,478, filed on Aug. 13, 2012.

(51) Int. Cl.
*A61B 17/22* (2006.01)
*A61B 17/3207* (2006.01)
(Continued)

(52) U.S. Cl.
CPC ........... *A61B 17/22012* (2013.01); *A61B 17/22* (2013.01); *A61B 17/3207* (2013.01); *A61M 25/007* (2013.01); *A61M 25/0013* (2013.01);
(Continued)

(58) Field of Classification Search
CPC .......... A61M 25/0032; A61M 25/007; A61M 25/0075; A61M 25/1036; A61M 25/10; A61M 25/003; A61M 2025/0079; A61M 2025/1013; A61M 2025/1052; A61M 2025/1061; A61B 2017/22034; A61B 2017/22054; A61B 2017/22067; A61B 2017/22079; A61B 2017/320716; A61B 2017/22084
See application file for complete search history.

(56) References Cited

U.S. PATENT DOCUMENTS 1,671,390 A 5/1928 Winning
1,920,006 A 7/1933 Dozier
(Continued)

FOREIGN PATENT DOCUMENTS

CN 200951252 Y 9/2007
GB 2484598 A 4/2012
(Continued)

OTHER PUBLICATIONS

Extended European Search Report on related European Application No. 13180183.9 dated Nov. 20, 2013.
(Continued)

*Primary Examiner* — Nathan R Price
*Assistant Examiner* — Justin L Zamory

(57) ABSTRACT

The apparatus includes a catheter having a combined infusion/aspiration lumen, a three lumen proximal portion and a two lumen distal portion. An infusion/aspiration valve located at the distal end of the catheter facilitates performing infusion and aspiration through the same lumen, which in turn reduces the number of lumens, and enables the combined infusion/aspiration lumen to be made larger without the need to increase the diameter of the catheter. Differing material properties in the proximal and distal portions of the catheter enable the proximal portion to be made stiffer for pushability, while the distal portion is more flexible to navigate tortuous vasculature and enable a greater amplitude agitator to be received within the catheter.

20 Claims, 10 Drawing Sheets

(51) Int. Cl.
  *A61M 25/00* (2006.01)
  *A61M 1/00* (2006.01)
  *A61M 25/10* (2013.01)

(52) U.S. Cl.
  CPC ....... *A61M 25/0032* (2013.01); *A61M 25/0075* (2013.01); *A61B 2017/22034* (2013.01); *A61B 2017/22054* (2013.01); *A61B 2017/22067* (2013.01); *A61B 2017/22079* (2013.01); *A61B 2017/22084* (2013.01); *A61B 2017/320716* (2013.01); *A61B 2217/005* (2013.01); *A61B 2217/007* (2013.01); *A61M 1/0058* (2013.01); *A61M 25/0023* (2013.01); *A61M 25/0054* (2013.01); *A61M 25/0069* (2013.01); *A61M 25/1011* (2013.01); *A61M 2025/0018* (2013.01); *A61M 2025/0079* (2013.01); *A61M 2025/1052* (2013.01)

(56) References Cited

U.S. PATENT DOCUMENTS

| | | |
|---|---|---|
| 3,503,400 A | 3/1970 | Osthagen et al. |
| 4,180,068 A | 12/1979 | Jacobsen et al. |
| 4,563,181 A | 1/1986 | Wijayarathna et al. |
| 4,680,026 A | 7/1987 | Weightman et al. |
| 4,758,235 A | 7/1988 | Tu |
| 4,850,240 A | 7/1989 | White |
| 4,927,418 A | 5/1990 | Dake et al. |
| 4,979,939 A | 12/1990 | Shiber |
| 5,002,625 A | 3/1991 | Naritomi et al. |
| 5,019,042 A | 5/1991 | Sahota |
| 5,019,054 A | 5/1991 | Clement et al. |
| 5,021,044 A | 6/1991 | Sharkawy |
| 5,034,000 A | 7/1991 | Freitas et al. |
| 5,059,178 A | 10/1991 | Ya |
| 5,069,662 A | 12/1991 | Bodden |
| 5,125,910 A | 6/1992 | Freitas |
| 5,147,377 A | 9/1992 | Sahota |
| 5,160,321 A | 11/1992 | Sahota |
| 5,160,559 A | 11/1992 | Scovil et al. |
| 5,186,714 A | 2/1993 | Boudreault et al. |
| 5,203,769 A | 4/1993 | Clement et al. |
| 5,224,929 A | 7/1993 | Remiszewski |
| 5,256,141 A | 10/1993 | Gencheff et al. |
| 5,279,546 A | 1/1994 | Mische et al. |
| 5,312,327 A | 5/1994 | Bales et al. |
| 5,320,604 A | 6/1994 | Walker et al. |
| 5,344,399 A | 9/1994 | DeVries |
| 5,347,992 A | 9/1994 | Pearlman et al. |
| 5,387,226 A | 2/1995 | Miraki |
| 5,397,307 A | 3/1995 | Goodin |
| 5,411,479 A | 5/1995 | Bodden |
| 5,425,723 A | 6/1995 | Wang |
| 5,439,454 A | 8/1995 | Lo et al. |
| 5,443,448 A | 8/1995 | DeVries |
| 5,474,533 A | 12/1995 | Ward et al. |
| 5,476,450 A | 12/1995 | Ruggio |
| 5,484,412 A | 1/1996 | Pierpont |
| 5,496,275 A | 3/1996 | Sirhan et al. |
| 5,498,236 A | 3/1996 | Dubrul et al. |
| 5,505,701 A | 4/1996 | Anaya Fernandez de Lomana |
| 5,516,336 A | 5/1996 | McInnes et al. |
| 5,554,119 A | 9/1996 | Harrison et al. |
| 5,558,642 A | 9/1996 | Schweich, Jr. et al. |
| 5,569,197 A | 10/1996 | Helmus et al. |
| 5,591,514 A | 1/1997 | Hirose et al. |
| 5,597,901 A | 1/1997 | Stern |
| 5,607,391 A | 3/1997 | Klinger et al. |
| 5,609,573 A | 3/1997 | Sandock |
| 5,665,063 A | 9/1997 | Roth et al. |
| 5,674,198 A | 10/1997 | Leone |
| 5,713,849 A | 2/1998 | Bosma et al. |
| 5,716,340 A | 2/1998 | Schweich, Jr. et al. |
| 5,718,677 A | 2/1998 | Capetan et al. |
| 5,743,875 A | 4/1998 | Sirhan et al. |
| 5,775,327 A | 7/1998 | Randolph et al. |
| 5,779,673 A | 7/1998 | Roth et al. |
| 5,833,644 A | 11/1998 | Zadno-Azizi et al. |
| 5,836,967 A | 11/1998 | Schneider |
| 5,902,299 A | 5/1999 | Jayaraman |
| 5,908,407 A | 6/1999 | Frazee et al. |
| 5,919,163 A | 7/1999 | Glickman |
| 5,925,013 A | 7/1999 | Exline et al. |
| 5,928,192 A | 7/1999 | Maahs |
| 5,928,203 A | 7/1999 | Davey et al. |
| 5,938,653 A | 8/1999 | Pepin |
| 6,013,069 A | 1/2000 | Sirhan et al. |
| 6,017,323 A | 1/2000 | Chee |
| 6,022,336 A | 2/2000 | Zadno-Azizi et al. |
| 6,027,475 A | 2/2000 | Sirhan et al. |
| 6,063,069 A | 5/2000 | Cragg et al. |
| 6,103,037 A | 8/2000 | Wilson |
| 6,120,904 A | 9/2000 | Hostettler et al. |
| 6,145,407 A | 11/2000 | Rottmann |
| 6,165,166 A | 12/2000 | Samuelson et al. |
| 6,165,199 A | 12/2000 | Barbut |
| 6,179,816 B1 | 1/2001 | Mottola et al. |
| 6,183,462 B1 | 2/2001 | Beals |
| 6,312,444 B1 | 11/2001 | Barbut |
| 6,319,244 B2 | 11/2001 | Suresh et al. |
| 6,322,577 B1 | 11/2001 | McInnes |
| 6,416,493 B1 | 7/2002 | Del Giglio |
| 6,436,077 B1 | 8/2002 | Davey et al. |
| 6,464,683 B1 | 10/2002 | Samuelson et al. |
| 6,485,500 B1 | 11/2002 | Kokish et al. |
| 6,503,353 B1 | 1/2003 | Peterson et al. |
| 6,524,296 B1 | 2/2003 | Beals |
| 6,533,763 B1 | 3/2003 | Schneiter |
| 6,544,220 B2 | 4/2003 | Shuman et al. |
| 6,569,146 B1 | 5/2003 | Werner et al. |
| 6,579,263 B1 | 6/2003 | Chernack |
| 6,579,277 B1 | 6/2003 | Rabiner et al. |
| 6,596,235 B2 | 7/2003 | Divino, Jr. et al. |
| 6,623,452 B2 | 9/2003 | Chien et al. |
| 6,652,491 B1 | 11/2003 | Walker et al. |
| 6,663,613 B1 | 12/2003 | Evans et al. |
| 6,676,650 B1 | 1/2004 | Magovern et al. |
| 6,679,861 B2 | 1/2004 | Yozu et al. |
| 6,692,461 B2 | 2/2004 | Wantink |
| 6,719,724 B1 | 4/2004 | Walker et al. |
| 6,749,619 B2 | 6/2004 | Ouriel et al. |
| 6,755,813 B2 | 6/2004 | Ouriel et al. |
| 6,790,196 B2 | 9/2004 | Kokate et al. |
| 6,849,068 B1 | 2/2005 | Bagaoisan et al. |
| 6,918,920 B1 * | 7/2005 | Wang ................ A61M 25/0069 606/194 |
| 6,923,787 B2 | 8/2005 | Wang |
| 6,929,633 B2 | 8/2005 | Evans et al. |
| 6,960,188 B2 | 11/2005 | Jorgensen |
| 6,960,189 B2 | 11/2005 | Bates et al. |
| 6,979,342 B2 | 12/2005 | Lee et al. |
| 7,022,106 B2 | 4/2006 | Jorgensen |
| 7,048,713 B2 | 5/2006 | Wang |
| 7,060,051 B2 | 6/2006 | Palasis |
| 7,066,873 B2 | 6/2006 | Hughett et al. |
| 7,094,245 B2 | 8/2006 | Adams et al. |
| 7,112,357 B2 | 9/2006 | Miller et al. |
| 7,172,572 B2 | 2/2007 | Diamond et al. |
| 7,223,253 B2 | 5/2007 | Hogendijk |
| 7,322,988 B2 | 1/2008 | Sterud et al. |
| 7,326,196 B2 | 2/2008 | Olsen et al. |
| 7,331,948 B2 | 2/2008 | Skarda |
| 7,367,967 B2 | 5/2008 | Eidenschink |
| 7,491,192 B2 | 2/2009 | DiFiore |
| 7,500,971 B2 | 3/2009 | Chang et al. |
| 7,515,957 B2 | 4/2009 | Doty et al. |
| 7,549,975 B2 | 6/2009 | Lee et al. |
| 7,575,568 B2 | 8/2009 | Holman et al. |
| 7,618,412 B2 | 11/2009 | Chernack |
| 7,641,638 B2 | 1/2010 | Waxman et al. |
| 7,641,757 B2 | 1/2010 | Kampa et al. |
| 7,645,261 B2 | 1/2010 | Hinchliffe |
| 7,678,075 B2 | 3/2010 | Wantink et al. |

(56) References Cited

U.S. PATENT DOCUMENTS

| | | | |
|---|---|---|---|
| 7,691,080 B2 | 4/2010 | Seward et al. | |
| 7,713,233 B2 | 5/2010 | Burgmeier et al. | |
| 7,763,010 B2 | 7/2010 | Evans et al. | |
| 7,766,049 B2 | 8/2010 | Miller et al. | |
| 7,815,599 B2 | 10/2010 | Griffin et al. | |
| 7,867,195 B2 | 1/2011 | Barbut et al. | |
| 7,914,486 B2 | 3/2011 | Chen et al. | |
| 7,955,365 B2 | 6/2011 | Doty | |
| 8,016,786 B2 | 9/2011 | Seward et al. | |
| 8,057,439 B2 | 11/2011 | Di Fiore | |
| 8,057,442 B2 | 11/2011 | Dikeman et al. | |
| 8,075,520 B2 | 12/2011 | Reznik | |
| 8,096,959 B2 | 1/2012 | Stewart et al. | |
| 8,100,881 B2 | 1/2012 | Hoffa | |
| 8,137,373 B2 | 3/2012 | Weber | |
| 8,162,879 B2 | 4/2012 | Hattangadi et al. | |
| 8,241,241 B2 | 8/2012 | Evans et al. | |
| 8,256,428 B2 | 9/2012 | Hindricks et al. | |
| 8,292,827 B2 | 10/2012 | Musbach et al. | |
| 2001/0041862 A1 | 11/2001 | Glickman | |
| 2002/0018866 A1 | 2/2002 | Lee et al. | |
| 2002/0052620 A1 | 5/2002 | Barbut | |
| 2002/0077595 A1 | 6/2002 | Hundertmark et al. | |
| 2002/0188276 A1* | 12/2002 | Evans | A61B 17/22 604/509 |
| 2003/0032921 A1 | 2/2003 | Duchamp | |
| 2003/0139751 A1 | 7/2003 | Evans et al. | |
| 2003/0199852 A1 | 10/2003 | Seward et al. | |
| 2004/0073158 A1 | 4/2004 | Shah et al. | |
| 2004/0197501 A1 | 10/2004 | Sridharan | |
| 2005/0043690 A1 | 2/2005 | Todd | |
| 2005/0096608 A1 | 5/2005 | Mannschedel et al. | |
| 2006/0064056 A1 | 3/2006 | Coyle et al. | |
| 2006/0064074 A1 | 3/2006 | Mallaby | |
| 2006/0149214 A1 | 7/2006 | Breiter et al. | |
| 2006/0200191 A1 | 9/2006 | Zadno-Azizi | |
| 2007/0005002 A1 | 1/2007 | Millman et al. | |
| 2007/0135763 A1 | 6/2007 | Musbach et al. | |
| 2007/0191812 A1 | 8/2007 | Nishide et al. | |
| 2007/0203563 A1 | 8/2007 | Hebert et al. | |
| 2008/0114286 A1 | 5/2008 | Hamel et al. | |
| 2008/0215034 A1 | 9/2008 | Clayton et al. | |
| 2008/0249463 A1 | 10/2008 | Pappone et al. | |
| 2008/0312671 A1 | 12/2008 | Riles et al. | |
| 2009/0005758 A1 | 1/2009 | Shah et al. | |
| 2009/0036831 A1 | 2/2009 | Howat | |
| 2009/0131827 A1 | 5/2009 | Crocker et al. | |
| 2009/0227944 A1 | 9/2009 | Weber | |
| 2009/0270796 A1 | 10/2009 | Perry et al. | |
| 2009/0270807 A1 | 10/2009 | Mas et al. | |
| 2009/0326439 A1 | 12/2009 | Chomas et al. | |
| 2010/0069881 A1 | 3/2010 | Salerno | |
| 2010/0082012 A1 | 4/2010 | Hattangadi et al. | |
| 2010/0152707 A1* | 6/2010 | Morris | A61M 1/008 604/523 |
| 2010/0268076 A1 | 10/2010 | Gat et al. | |
| 2010/0286766 A1 | 11/2010 | Ye | |
| 2010/0312222 A1 | 12/2010 | Leeflang et al. | |
| 2011/0015564 A1 | 1/2011 | Bonnette et al. | |
| 2011/0034863 A1 | 2/2011 | Hoffa | |
| 2011/0046542 A1 | 2/2011 | Evans et al. | |
| 2011/0046549 A1 | 2/2011 | Waysbeyn et al. | |
| 2011/0106132 A1 | 5/2011 | Barbut et al. | |
| 2011/0208022 A1 | 8/2011 | Brawer et al. | |
| 2011/0218494 A1 | 9/2011 | Gerrans et al. | |
| 2011/0224600 A1 | 9/2011 | Orlandi | |
| 2011/0230823 A1 | 9/2011 | Simonsen | |
| 2011/0270228 A1 | 11/2011 | Haslinger et al. | |
| 2011/0295114 A1 | 12/2011 | Agah et al. | |
| 2011/0313353 A1 | 12/2011 | Seward et al. | |
| 2012/0078096 A1* | 3/2012 | Krolik | A61B 17/22032 600/435 |
| 2012/0089167 A1 | 4/2012 | Barbut | |
| 2012/0101434 A1 | 4/2012 | Stewart et al. | |
| 2012/0259215 A1 | 10/2012 | Gerrans et al. | |
| 2012/0302953 A1 | 11/2012 | Don Michael | |
| 2012/0303011 A1 | 11/2012 | Schaeffer | |

FOREIGN PATENT DOCUMENTS

| | | |
|---|---|---|
| WO | WO 98/43531 A1 | 10/1998 |
| WO | WO 99/19016 A1 | 4/1999 |
| WO | WO 01/54754 A1 | 8/2001 |
| WO | WO 2004/037178 | 5/2004 |

OTHER PUBLICATIONS

Office Action on related JP Application No. 2013-167442 from the Japanese Patent Office (JPO) dated Jun. 16, 2014.
Notice of Preliminary Rejection, and translation thereof, from counterpart Korean Patent Application No. 10-2013-95758, dated Oct. 2, 2014, 9 pp.
Office Action from U.S. Appl. No. 13/835,812, dated May 11, 2015, 11 pp.
Office Action from U.S. Appl. No. 13/835,812, dated Nov. 4, 2015, 11 pp.

* cited by examiner

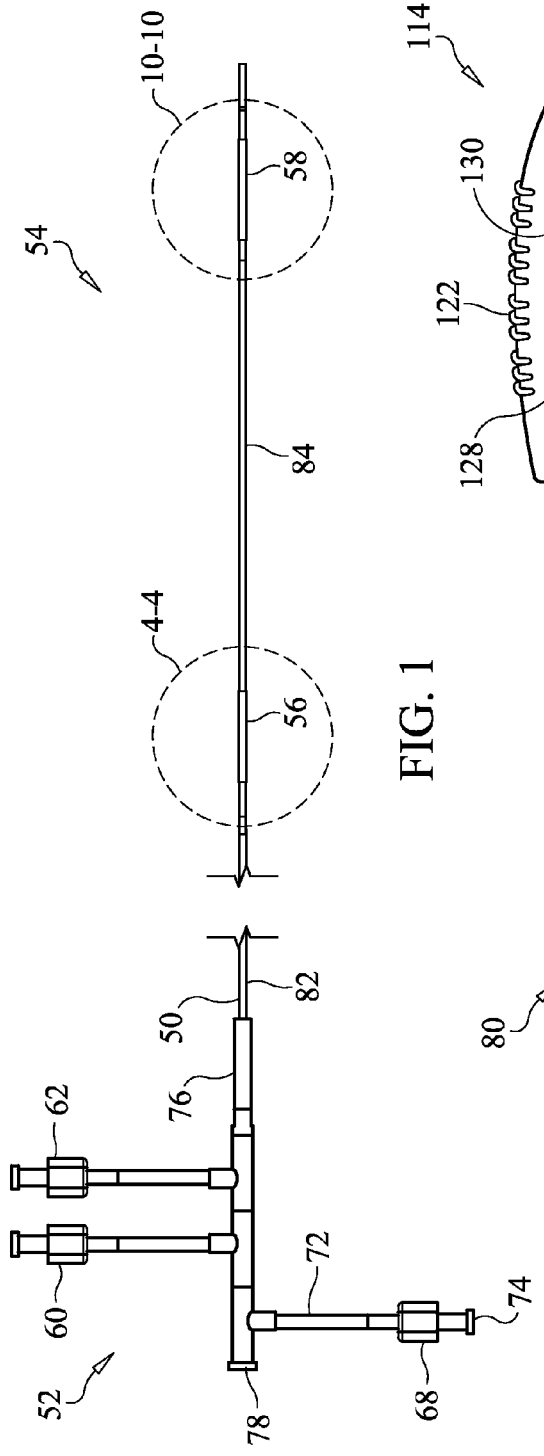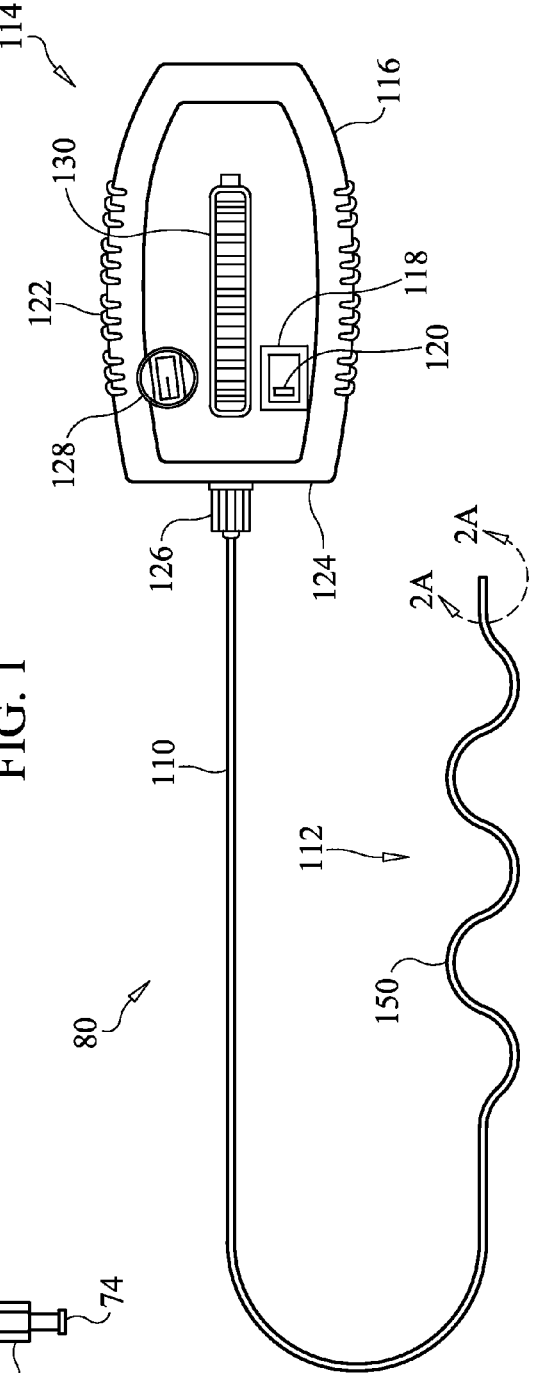

APPARATUS AND METHODS FOR CLOT DISRUPTION AND EVACUATION

CROSS-REFERENCE TO RELATED APPLICATION

This application claims priority to provisional application Ser. No. 61/682,478, filed on Aug. 13, 2012, the entire contents of which are hereby incorporated by reference.

TECHNICAL FIELD

The present embodiments relate to apparatus and methods for disrupting and evacuating occlusive material from blood vessels.

BACKGROUND

Thrombosis and atherosclerosis are ailments that result from deposition of thrombus or atheromas, respectively, in the luminal walls of blood vessels. When hardened, such deposits typically result in vascular obstruction and reduced blood flow through the lumens of affected blood vessels. Thrombosis and atherosclerosis are most common in the peripheral blood vessels that feed the limbs of the human body, and the coronary arteries, which feed the heart. Stasis, incompetent valves, and trauma in the venous circulation cause thrombosis, particularly occurring as a deep vein thrombosis in the peripheral vasculature. When such deposits accumulate in localized regions of the blood vessel, they can restrict blood flow and cause a serious health risk.

In addition to forming in the natural vasculature, thrombosis is a serious problem in "artificial" blood vessels or autologous blood vessel grafts, particularly in peripheral femoral-popliteal and coronary bypass grafts and dialysis access grafts and fistulas. The creation of such artificial blood vessels requires anastomotic attachment at at least one, and usually at at least two, locations in the vasculature. Such sites of an anastomotic attachment are particularly susceptible to thrombus formation due to narrowing caused by intimal hyperplasia, and thrombus formation at these sites is a frequent cause of failure of the implanted graft or fistula. The arterio-venous grafts and fistulas that are used for dialysis access are significantly compromised by thrombosis at the sites of anastomotic attachment and elsewhere. Thrombosis often occurs to such an extent that the graft needs to be replaced within a few years or, in the worst cases, a few months.

A variety of methods have been developed for treating thrombosis and atherosclerosis in the coronary and peripheral vasculature, as well as in implanted grafts and fistulas. Such techniques include surgical procedures, such as coronary artery bypass grafting, and minimally invasive procedures, such as angioplasty, atherectomy, thrombectomy, thrombolysis, transmyocardial revascularization, etc.

Some techniques for treating thrombosis and atherosclerosis include dissolving clots using thrombolytic agents. Examples of thrombolytic agents include tissue plasminogen activator (tPA), streptokinase, urokinase, etc. Such thrombolytic agents may be delivered systemically or locally. When delivered locally, the treatment may be coupled with mechanical disruption of the clot and evacuation from the vessel lumen.

SUMMARY

The various embodiments of the present apparatus and methods for clot disruption and evacuation have several features, no single one of which is solely responsible for their desirable attributes. Without limiting the scope of the present embodiments as expressed by the claims that follow, their more prominent features now may be discussed briefly. After considering this discussion, and particularly after reading the section entitled "Detailed Description," one will understand how the features of the present embodiments provide the advantages described herein.

Many of the present embodiments are described as including various combinations of features and/or components. It should be understood that these combinations are merely examples. Additional embodiments may comprise combinations of features and/or components different from those described here. For example, certain features and/or components may be omitted from various embodiments and/or combined with features and/or components shown in other combinations herein.

The present embodiments provide apparatus, methods, and kits for disrupting and dissolving thrombus present in a patient's vasculature. The thrombus, also referred to as clot, may be present in both the arterial and venous vasculature, as well as the peripheral venous vasculature, and grafts. The present embodiments are particularly suited for treating thrombotic disease within the venous vasculature, such as thrombosis in the superficial veins, the central veins, the femoral-popliteal veins, the iliofemoral vein, etc. The present embodiments are also particularly suited for treating arterial thrombotic disease, such as thrombosis in the iliofemoral artery, the superficial femoral artery, etc.

The present embodiments provide apparatus and methods for infusing thrombolytic agents, aspirating dissolved clot, and any solid clot that may be present, and passing a guide wire, all through a common catheter lumen. Other embodiments may provide for separate lumens for infusing, aspirating and/or passing a guide wire. Embodiments with fewer lumens may provide the additional advantage of having a relatively small diameter compared to other devices.

In a first aspect, apparatus for disrupting clot over a luminal length of a blood vessel according to the present embodiments comprises a catheter body having a proximal end, a distal end and at least one lumen. At least one opening along a treatment length of the catheter body allows infusion of a thrombolytic agent and/or aspiration of dissolved clot, and any solid clot that may be present. The catheter body further includes at least one radially expandable body for inhibiting flow of clot beyond the luminal length of the blood vessel.

The dimensions and materials of the catheter body may be selected according to characteristics of a treatment site within the vasculature to be treated. For example, the catheter may be sized to be introduced percutaneously or via a cut down to the vasculature at an entry, and then be intravascularly advanced, typically over a guide wire, to the treatment site. Treatment sites in the peripheral, coronary, and cerebral vasculature may generally be approached through different access sites, and may require catheters having different lengths, diameters, and flexibilities.

The luminal length of the blood vessel to be treated may be at least 3 cm, at least 10 cm, in the range from 3 cm to 100 cm, and usually from 5 cm to 55 cm. The length of thrombotic disease being treated may vary depending on the location of the disease within the vasculature. For example, deep vein thrombosis is often spread over a length in the range from 5 cm to 100 cm. The apparatus and methods of the present embodiments are capable of treating disease spread over these lengths as described in more detail below.

The apparatus of the present embodiments need not be adapted to treat the entire length of the diseased region at once. It will often be possible and in some cases desirable to treat discrete lengths within the entire diseased region separately. Such discrete lengths may be treated successively, e.g., by axially translating the treatment device within the blood vessel being treated. Alternatively, the segments could be treated using different devices, optionally introduced from different introduction sites in the vasculature.

When the blood vessel is a vein, the target site may be selected from the vena cava, the iliac vein, the femoral vein, the popliteal vein, the common iliac vein, the external iliac vein, the brachial vein, the subclavian vein, or any other vein. When the target blood vessel is an artery, the target site may be selected from the internal iliac artery, the external iliac artery, the popliteal artery, the coronary arteries, the superficial femoral artery, the brachial artery, or any other artery.

In various embodiments, the at least one opening in the treatment length of the catheter may include one opening in a side wall of the lumen of the catheter body, multiple smaller spaced-apart openings in the lumen, a combination of multiple smaller openings and one larger opening, etc. Generally, the at least one opening may have any suitable configuration for infusing an agent and/or aspirating dissolved clot, and any solid clot that may be present.

Some of the present embodiments further include a mechanical agitator along the treatment length of the catheter body for mechanically agitating clot at the treatment site and/or for dispersing lytic at the treatment site. The mechanical agitator may have a wide variety of specific configurations. For example, the mechanical agitator may comprise a radially expansible agitator that is rotatable and/or axially translatable within the catheter body. In certain embodiments, the radially expansible agitator may be self-expanding. For example, it may comprise a resilient element that may be radially constrained to have a low profile (small diameter) and may be freed from radial constraint to have an enlarged profile (large diameter) with a non-linear geometry. Radial constraint may be provided by a sleeve or sheath that may be axially advanced and retracted relative to the catheter body to cover and uncover the radially expansible agitator. In this way, the catheter may be introduced to a treatment site within the vasculature with the expansible agitator covered (and thus radially constrained). After the desired treatment site is reached, the sheath or sleeve may be axially retracted to release the radially expansible agitator so that it expands to engage the clot in the blood vessel. The agitator may then be rotated and/or axially translated to engage and disrupt the clot in combination with the release of a thrombolytic agent, as described in more detail below. Such rotation, oscillation, and/or translation may be performed using a motor drive unit operatively connected to the agitator, or may be performed manually in whole or in part.

In an alternative embodiment, the radially expansible agitator may comprise a resilient element that may be axially shortened to assume an enlarged profile having a non-linear geometry. For example, a self-expanding resilient element may be straightened (tensioned) by initially positioning a rod or stylet therein in order to lengthen the element and cause it to straighten to a low profile diameter. The agitator may then be expanded by retracting the rod or stylet to release the agitator from tension and permit the agitator to radially expand as a result of the agitator's inherent spring force. Alternatively, the agitator may be formed to have a generally straight, low profile configuration and be actively caused to radially expand by pulling on a rod or wire to cause axial shortening.

The agitator may have a variety of specific geometries, such as a helical geometry, a spiral geometry, a serpentine geometry, a zig-zag geometry, an alternating helix geometry (e.g., two or more helical geometries in tandem where successive helixes are wound in opposite directions), and/or a variety of other random geometries. The geometries may be such that the resilient element can engage against and penetrate into the clot within a blood vessel as the resilient element is radially expanded. As the resilient element is thereafter rotated and/or axially translated, the element then mechanically engages and disrupts the clot. By simultaneously introducing the thrombolytic agent directly to the region that is being mechanically engaged by the agitator, disruption and dissolution of the clot is significantly enhanced.

In the present embodiments that include a mechanical agitator, the apparatus may be configured to release the thrombolytic agent along substantially the entire length of the agitator that is in contact with the clot to be disrupted. In this way, the thrombolytic agent may be released at the point of mechanical agitation, resulting in both improved distribution of the thrombolytic agent into the clot as well as improved disruption and dissolution of the clot.

In certain embodiments, the agitator may be configured as a tube having a thrombolytic agent delivery lumen therein. The tube may have agent delivery ports and/or porous regions to permit the release of the thrombolytic agent at the treatment site. In this way, the thrombolytic agent may be delivered while the agitator is deployed within the catheter.

The clot disruption and dissolution apparatus of the present embodiments may further comprise means for isolating at least one end of the treatment site to reduce blood flow through the region being treated. For example, at least one balloon may be provided on the catheter body distally or proximally of the agitator and thrombolytic agent distribution region. When only a single balloon is used for isolation, it is preferably downstream from the treatment site. This arrangement inhibits the loss of the thrombolytic agent as well as the release of emboli downstream. Preferably, isolation means are provided on both the distal and proximal sides of the agitator and thrombolytic agent distribution region. The isolation means may comprise a pair of axially spaced-apart balloons disposed on the catheter body. Optionally, one of the balloons is disposed on a separate, telescoping portion of the catheter body in order to permit length adjustment of the region to be isolated. Alternatively, a variety of other isolation means, such as deployable flanges, malecot structures, expansible braids, etc, could also be employed.

In another apparatus aspect, the present embodiments provide an apparatus for disrupting clot over a target region of a blood vessel. The apparatus comprises a catheter body having a proximal end and a distal end. An agitator is disposed near the distal end for mechanically agitating clot over the target region. A port near the distal end is in fluid communication with an agent supply source for distributing an agent along the target region.

In many embodiments, the agent will comprise a thrombolytic agent, which may provide an enzymatic action to break down fibrin clot matrix. A variety of other agents may also be used, including group IIb/IIIa Inhibitors (to inhibit fibrinogen binding site of platelet membrane), other antiplatelet agents, anti-thrombin agents and agents directed toward prevention of restenosis (which may inhibit coagulation and/or inhibit restenosis by decreasing smooth muscle proliferation and migration), gene therapeutic agents (for preventing restenosis and promoting angiogenesis), chemotherapeutic agents (generally designed to treat malignancies), imaging media, and/or other potential agents.

The methods of the present embodiments allow for a wide variety of particular treatment protocols. For example, the agitator may be driven at different and/or variable speeds. The agitator may be rotated and/or oscillated at speeds in the range from 0 rpm to 50,000 rpm, preferably from 50 rpm to 5,000 rpm. The speeds may be set and/or adjusted at a wide variety of particular rotational speeds within these ranges. In some cases, the direction of the rotation may be reversed during the course of the procedure. The agitator may further be axially advanced or retracted during the course of treatment to enhance the disruption of the clot and introduction of the thrombolytic into the clot.

The treatment methods of the present embodiments may further comprise aspiration of the disrupted clot from the treatment site. Aspiration may be accomplished using a lumen or lumens within the sheath and/or agitator to withdraw the disrupted clot. Optionally, mechanical means, such as an Archimedes screw or other pump, may be incorporated into the catheter to enhance the aspiration and removal of the disrupted clot. In other embodiments, such a pump may be mounted to a separate structure, such as to a sheath removably disposed over the catheter, an inner structure removably disposed within a lumen of the catheter, etc. Still further embodiments may rely on an aspiration means that remains outside the patient, such as a syringe, vacuum container, etc.

In some embodiments, blood may be periodically or continuously introduced into the treatment region, tPA acts on plasminogen within the vasculature to breakup thrombus. If the treatment region of the present embodiments are isolated, it may be beneficial to introduce fresh blood containing plasma in order to enhance the activity of the thrombolytic agent, particularly tPA. Most simply, fresh blood could be introduced by periodically opening an isolation balloon that isolates the treatment region.

The methods of the present embodiments can rely on two or more of the treatment catheters to be used simultaneously. For example, in the treatment of arterio-venous grafts, it is possible to introduce two treatment catheters according to the present embodiments, each of which has a balloon or other occlusion device at its distal end, to an A-V graft at a point near its middle. By introducing the two treatment catheters in opposite directions, the graft may be isolated very close to the points at which it is anastomosed to the natural vasculature. After such isolation is achieved, the interior of the A-V graft can then be cleaned out according to the methods of the present embodiments, and preferably the released clot and thrombus may be withdrawn through an access sheath to the A-V graft.

The present embodiments still further comprise kits, including a catheter having an agitator and a thrombolytic agent delivery means. The kits further include instructions for use according to any of the methods set forth above and/or below. In addition to the catheter and the instructions for use, the kits may further comprise packaging, such a box, pouch, tray, tube, bag, etc. that holds the catheter and the instructions for use. The catheter may be maintained sterile within the package, and the instructions for use may be printed on a separate package insert or piece of paper. Alternatively, the instructions for use may be printed in whole or in part on a portion of the packaging.

One of the present embodiments comprises apparatus for disrupting a clot in a blood vessel, the apparatus comprising: a catheter body having a proximal length and a treatment length; at least one port along the proximal length of the catheter body; at least one infusion opening along the treatment length of the catheter body; at least one aspiration opening along the treatment length of the catheter body; a first lumen within the catheter body in fluid communication with the infusion opening and in fluid communication with the aspiration opening; a valve member along the treatment length of the catheter body, the valve being configured to selectively open and close fluid communication between the port and the aspiration opening; and an agitator that is translatable longitudinally within the first lumen. In a further aspect of the present embodiment, the valve member comprises a body that is translatable longitudinally within the first lumen. In a further aspect of the present embodiment, the body comprises a first position located proximally of the aspiration opening and a second position located distally of the aspiration opening. In a further aspect of the present embodiment, when the body is in the first position the apparatus is configured to infuse a thrombolytic agent into the vessel through the first lumen and the infusion opening, and when the body is in the second position the apparatus is configured to aspirate dissolved clot, and any solid clot that may be present, from the vessel through the aspiration opening and the first lumen. A further aspect of the present embodiment comprises an aspiration source; wherein when the body is in the first position the body substantially blocks fluid communication within the first lumen between the aspiration opening and the aspiration source, and when the body is in the second position the body does not block fluid communication within the first lumen between the aspiration opening and the aspiration source. A further aspect of the present embodiment comprises an infusion source; wherein when the body is in the first position the body substantially blocks fluid communication within the first lumen between the aspiration opening and the infusion source, the body therefore being configured to cause fluid flowing from the infusion source to flow out of the first lumen through the at least one infusion opening. In a further aspect of the present embodiment, the agitator comprises an elongate member having a non-linear portion along the treatment length of the catheter body. In a further aspect of the present embodiment, the body is located in a distal portion of the agitator and is translatable therewith along the first lumen. A further aspect of the present embodiment comprises a first expandable member along the treatment length of the catheter body, the first expandable member defining a first expandable internal volume. A further aspect of the present embodiment comprises a second lumen within the catheter body in fluid communication with the first expandable internal volume of the first expandable member. A further aspect of the present embodiment comprises a second expandable member along the treatment length of the catheter body, the second expandable member defining a second expandable internal volume. A further aspect of the present embodiment comprises a third lumen within the catheter body in fluid communication with the second expandable internal volume of the second expandable member. In a further aspect of the present embodiment, the second lumen terminates at the first expandable internal volume of the first expandable member and the third lumen terminates at the second expandable internal volume of the second expandable member. In a further aspect of the present embodiment, the infusion opening and the aspiration opening are located between the first and second expandable members. In a further aspect of the present embodiment, the at least one infusion opening comprises a plurality of infusion openings that are spaced radially around the catheter body, over a radial span of greater than 180° about the longitudinal axis of the catheter body. In a further aspect of the present embodiment, the infusion openings are located on a portion of the catheter body that comprises no lumens other than the first lumen and the second lumen, the first lumen and the second lumen being collectively sufficient to facilitate infusion through the infusion openings, aspiration through the aspiration opening, and expansion of one of the expandable members. In a further aspect of the present embodiment, the catheter body comprises a proximal portion and a distal portion secured to one another at a joint, and the first expandable member surrounds the joint. In a further aspect of the present embodiment, the joint is a butt joint. In a further aspect of the present embodiment, the at least one infusion opening comprises a plurality of infusion openings, and the infusion openings are spaced from one another both radially and longitudinally with respect to the treatment length of the catheter body. In a further aspect of the present embodiment, the infusion openings are grouped in groups of three, with each group of three infusion openings being located at a same position along the treatment length of the catheter body. In a further aspect of the present embodiment, the infusion openings in each group of three infusion openings are uniformly radially spaced 120° from one another. In a further aspect of the present embodiment, the agitator is configured to mechanically disrupt the clot and/or to disperse lytic to facilitate dissolving the clot.

Another of the present embodiments comprises apparatus for disrupting a clot in a blood vessel, the apparatus comprising: a catheter body having a proximal length and a treatment length; at least one port along the proximal length of the catheter body; at least one infusion opening along the treatment length of the catheter body; at least one aspiration opening along the treatment length of the catheter body; a first lumen within the catheter body in fluid communication with the infusion opening and in fluid communication with the aspiration opening; means for selectively opening and closing fluid communication between the port and the aspiration opening; and an agitator that is translatable longitudinally within the first lumen. In a further aspect of the present embodiment, the means includes a body portion located within the first lumen. In a further aspect of the present embodiment, the body portion is translatable longitudinally between a first position located proximally of the aspiration opening and a second position located distally of the aspiration opening. In a further aspect of the present embodiment, when the body portion is in the first position the apparatus is configured to infuse a thrombolytic agent into the vessel through the first lumen and the infusion opening, and when the body portion is in the second position the apparatus is configured to aspirate dissolved clot, and any solid clot that may be present, from the vessel through the aspiration opening and the first lumen. A further aspect of the present embodiment comprises an aspiration source; wherein when the body is in the first position the body substantially blocks fluid communication within the first lumen between the aspiration opening and the aspiration source, and when the body is in the second position the body does not block fluid communication within the first lumen between the aspiration opening and the aspiration source. A further aspect of the present embodiment comprises an infusion source; wherein when the body is in the first position the body substantially blocks fluid communication within the first lumen between the aspiration opening and the infusion source, the body therefore being configured to cause fluid flowing from the infusion source to flow out of the first lumen through the at least one infusion opening. In a further aspect of the present embodiment, the agitator comprises an elongate member having a non-linear portion along the treatment length of the catheter body. In a further aspect of the present embodiment, the body portion is located in a distal portion of the agitator and is translatable therewith along the first lumen. In a further aspect of the present embodiment, the at least one infusion opening comprises a plurality of infusion openings that are spaced radially around the catheter body, over a radial span of greater than 180° about the longitudinal axis of the catheter body. In a further aspect of the present embodiment, the infusion openings are located on a portion of the catheter body that comprises no lumens other than the first lumen and a second lumen, the first lumen and the second lumen being collectively sufficient to facilitate infusion through the infusion openings, aspiration through the aspiration opening, and expansion of one of the expandable members. In a further aspect of the present embodiment, the agitator is configured to mechanically disrupt the clot and/or to disperse lytic to facilitate dissolving the clot.

Another of the present embodiments comprises apparatus for disrupting a clot in a blood vessel, the apparatus comprising: a catheter body having a proximal length and a treatment length; at least one port along the proximal length of the catheter body; at least a first opening along the treatment length of the catheter body; a first lumen within the catheter body in fluid communication with the opening; a body member axially translatable within the first lumen between a first position located proximally of the opening and a second position located distally of the opening; and an agitator that is translatable longitudinally within the first lumen. In a further aspect of the present embodiment, when the body member is in the first position fluid communication between the port and the opening is closed, and when the body member is in the second position fluid communication between the port and the opening is open. In a further aspect of the present embodiment, the agitator comprises an elongate member having a non-linear portion along the treatment length of the catheter body. In a further aspect of the present embodiment, the body member is located in a distal portion of the agitator and is translatable therewith along the first lumen. A further aspect of the present embodiment comprises at least a second opening along the treatment length of the catheter body. In a further aspect of the present embodiment, the first opening is configured for aspiration of dissolved clot, and any solid clot that may be present, from within the vessel and the second opening is configured for infusion of a thrombolytic agent into the vessel. A further aspect of the present embodiment comprises an aspiration source; wherein when the body is in the first position the body substantially blocks fluid communication within the first lumen between the aspiration opening and the aspiration source, and when the body is in the second position the body does not block fluid communication within the first lumen between the aspiration opening and the aspiration source. A further aspect of the present embodiment comprises an infusion source; wherein when the body is in the first position the body substantially blocks fluid communication within the first lumen between the aspiration opening and the infusion source, the body therefore being configured to cause fluid flowing from the infusion source to flow out of the first lumen through the at least one infusion opening. In a further aspect of the present embodiment, the agitator is configured to mechanically disrupt the clot and/or to disperse lytic to facilitate dissolving the clot.

Another of the present embodiments comprises a method for disrupting a clot at a treatment location in a blood vessel, the method comprising: positioning a treatment length of a catheter body at the treatment location; positioning a valve body, also called an occluding body, within a first lumen of the catheter body proximally of an aspiration opening in a sidewall of the catheter body, the aspiration opening being located along the treatment length of the catheter body; infusing a thrombolytic agent into the vessel through the lumen and at least one infusion opening located along the treatment length of the catheter body; activating an agitating mechanism located along the treatment length of the catheter body to disrupt the clot and to disperse lytic at the treatment site; advancing the occluding body within the first lumen of the catheter body until it is positioned distally of the aspiration opening; and aspirating dissolved clot, and any solid clot that may be present, from the vessel through the aspiration opening and the first lumen. In a further aspect of the present embodiment, the agitating mechanism comprises an elongate member having a non-linear portion along the treatment length of the catheter body. In a further aspect of the present embodiment, activating the agitating mechanism comprises rotating and/or axially translating the agitating mechanism within the blood vessel and against the clot. In a further aspect of the present embodiment, the occluding body is located in a distal portion of the agitating mechanism, and advancing the occluding body within the first lumen comprises advancing the agitating mechanism. In a further aspect of the present embodiment, wherein positioning the occluding body proximally of the aspiration opening further comprises directing fluid flow from an infusion source through the infusion opening and not through the aspiration opening. A further aspect of the present embodiment comprises expanding a first expandable member located along the treatment length of the catheter body until the vessel is occluded by the first expandable member. A further aspect of the present embodiment comprises expanding a second expandable member located along the treatment length of the catheter body until the vessel is occluded by the second expandable member, wherein the first and second expandable members are located on either side of the clot. In a further aspect of the present embodiment, expanding the first expandable member comprises introducing fluid into a first expandable internal volume of the first expandable member through a second lumen of the catheter body. In a further aspect of the present embodiment, expanding the second expandable member comprises introducing fluid into a second expandable internal volume of the second expandable member through a third lumen of the catheter body. In a further aspect of the present embodiment, the second lumen terminates at the first expandable internal volume of the first expandable member and the third lumen terminates at the second expandable internal volume of the second expandable member. In a further aspect of the present embodiment, the infusion opening and the aspiration opening are located between the first and second expandable members. In a farther aspect of the present embodiment, the catheter body comprises a proximal portion and a distal portion secured to one another at a joint, and the first expandable member surrounds the joint. In a further aspect of the present embodiment, the joint is a butt joint. In a further aspect of the present embodiment, infusing the thrombolytic agent comprises forming a plurality of outflows of the infused agent that are spaced radially around the catheter body, over a radial span of greater than 180° about the longitudinal axis of the catheter body. In a further aspect of the present embodiment, the outflows are formed along a portion of the catheter body that comprises the first lumen and a second lumen; further comprising achieving infusion via the plurality of outflows, aspiration through the aspiration opening, and expansion of an expandable member, all by using no catheter body lumens other than the first lumen and the second lumen. In a further aspect of the present embodiment, the at least one infusion opening comprises a plurality of infusion openings, and the infusion openings are spaced from one another both radially and longitudinally with respect to the treatment length of the catheter body. In a further aspect of the present embodiment, the infusion openings are grouped in groups of three, with each group of three infusion openings being located at a same position along the treatment length of the catheter body. In a further aspect of the present embodiment, the infusion openings in each group of three infusion openings are uniformly radially spaced 120° from one another.

Another of the present embodiments comprises a method for disrupting a clot at a treatment location in a blood vessel, the method comprising: positioning a treatment length of a catheter body at the treatment location, the catheter body having a lumen, an aspiration opening in a sidewall thereof along the treatment length of the catheter body, and at least one port along a proximal length of the catheter body; closing fluid communication between the port and the aspiration opening through the lumen; infusing a thrombolytic agent into the vessel through the lumen and at least one infusion opening located along the treatment length of the catheter body; activating an agitating mechanism located along the treatment length of the catheter body to disrupt the clot; closing fluid communication between the port and the aspiration opening through the lumen; and aspirating dissolved clot, and any solid clot that may be present, from the vessel through the aspiration opening and the lumen. In a further aspect of the present embodiment, the agitating mechanism comprises an elongate member having a non-linear portion along the treatment length of the catheter body. In a further aspect of the present embodiment, activating the agitating mechanism comprises rotating and/or axially translating the agitating mechanism within the blood vessel and against the clot.

BRIEF DESCRIPTION OF THE DRAWINGS

The various embodiments of the present apparatus and methods for clot disruption and evacuation now may be discussed in detail with an emphasis on highlighting the advantageous features. These embodiments depict the novel and non-obvious apparatus and methods shown in the accompanying drawings, which are for illustrative purposes only. These drawings include the following figures, in which like numerals indicate like parts:

FIG. 1 is a top plan view of a catheter for use in an apparatus for clot disruption and evacuation, and lytic distribution, according to one of the present embodiments;

FIG. 2 is a top plan view of an agitator for use in an apparatus for clot disruption and evacuation, and lytic distribution, according to one of the present embodiments;

DETAILED DESCRIPTION

Figure 3:
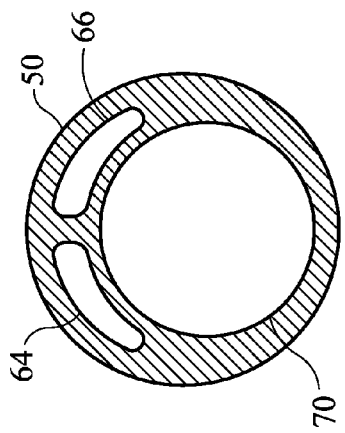
FIG. 3 is a cross-sectional view of the apparatus of FIG. 3 taken along the line 3-3.

The following detailed description describes the present embodiments with reference to the drawings. In the drawings, reference numbers label elements of the present embodiments. These reference numbers are reproduced below in connection with the discussion of the corresponding drawing features.

The embodiments of the present apparatus and methods for clot disruption and evacuation are described below with reference to the figures. These figures, and their written descriptions, indicate that certain components of the apparatus are formed integrally, and certain other components are formed as separate pieces. Components shown and described herein as being formed integrally may in alternative embodiments be formed as separate pieces. Components shown and described herein as being formed as separate pieces may in alternative embodiments be formed integrally. Further, as used herein the term integral describes a single unitary piece.

Directional terms used herein, such as proximal, distal, upper, lower, clockwise, counterclockwise, etc., are used with reference to the configurations shown in the figures. For example, a component that is described as rotating clockwise when viewed from the perspectives shown in the figures may be described as rotating counterclockwise when viewed from the opposite perspective. Furthermore, the present embodiments may be modified by altering or reversing the positions or directions of movement of various components. Accordingly, directional terms used herein should not be interpreted as limiting.

FIGS. 1 and 2 illustrate one embodiment of apparatus for disrupting a clot in a blood vessel. With reference to FIG. 1, the apparatus comprises a catheter body 50 having a proximal length 52 and a treatment length 54. A proximal balloon 56 and a distal balloon 58 are located along the treatment length 54, and define proximal and distal ends, respectively, of the treatment length 54. The proximal length 52 includes a plurality of ports, including a proximal balloon inflation port 60 and a distal balloon inflation port 62. With reference to FIG. 3, the proximal balloon inflation port 60 is in fluid communication with an interior of the proximal balloon 56 through a proximal balloon inflation lumen 64 that extends through the catheter body 50 between the port 60 and the balloon 56. The distal balloon inflation port 62 is in fluid communication with an interior of the distal balloon 58 through a distal balloon inflation lumen 66 that extends through the catheter body 50 between the port 62 and the balloon 58, and which is preferably separate from, and not in fluid communication with, the proximal balloon inflation lumen 64. With reference to FIG. 1, the proximal length 52 further includes an infusion/aspiration port 68 that is in fluid communication with a plurality of infusion openings and an aspiration opening (shown in later figures) located along the treatment length 54 through a combined infusion/aspiration lumen 70 (FIG. 3) that extends through the catheter body 50 from the port 68 to the openings.

With continued reference to FIG. 1, each of the ports 60, 62, 68 can include an elongate tubular portion 72 that extends perpendicularly from the catheter body 50. In alternative embodiments, the tubular portions 72 may extend from the catheter body 50 at a non-perpendicular angle. The balloon inflation ports 60, 62 are located adjacent one another on a first side of the catheter body 50, and the infusion/aspiration port 68 is located on a second, opposite, side of the catheter body 50 and proximally of the balloon inflation ports 60, 62. However, the illustrated arrangement of the ports 60, 62, 68 is just one example, and other arrangements can be employed. At an end of each of the tubular portions 72 spaced from the catheter body 50, each port includes a connector 74 configured to receive an infusion/aspiration device, such as a syringe (not shown). For example, the connector 74 may comprise a Luer-type connector, such as a LUER-LOK® connector or a LUER-SLIP connector.

The proximal length 52 of the catheter body 50 can further comprise a substantially rigid tubular section 76 from which each of the ports 60, 62, 68 extends. A proximal end of the rigid section includes a connector 78 configured to receive an agitator 80, which is described below and illustrated in FIG. 2. For example, the connector 78 may comprise a Luer-type connector, such as a LUER-LOK® connector. The combined infusion/aspiration lumen 70 can extend through the proximal end of the tubular section 76, i.e. the proximal end includes an opening corresponding to the location of the infusion/aspiration lumen 70. However, the balloon inflation lumens 64, 66 need not extend to the proximal end. Rather, these lumens can be closed at their respective proximal ends to facilitate maintaining pressure within the balloons 56, 58 when they are inflated.

With continued reference to FIG. 1, and as described in further detail below, the catheter body 50 comprises a proximal section 82 and a distal section 84. The proximal section 82 extends from the proximal end to a location beneath the proximal balloon 56 (illustrated in further detail below). The distal section 84 is joined to a distal end of the proximal section 82, and extends to a distal end of the catheter body 50. As detailed further below, the proximal and distal sections 82, 84 can have different cross-sectional configurations, and may be formed of different materials and/or may have different dimensions. In certain embodiments, for example, the proximal section 82 may have a greater stiffness than the distal section 84, such that the proximal section 82 is configured for pushability while the distal section 84 is adapted for navigating tortuous vasculature.

The catheter body 50 is preferably sized and configured to be advanced through a patient's vasculature from a transcutaneous access site to a treatment site within the vasculature. Example dimensions for the catheter body 50 include an outside diameter of approximately 8 French, or in the range of 4 French to 12 French, or outside diameters of 0.095-0.097 inches and 0.085-0.087 inches for the proximal and distal sections, respectively; and a length in the range of 50 cm-200 cm, or about 80 cm, or about 120 cm. Material(s) from which the catheter body 50 is constructed is preferably rigid enough to allow the catheter 50 to be pushed distally, but flexible enough to enable navigation of tortuous vasculature. Example materials for the proximal section 82 include polyether block amide (PEBAX™), or any lubricious and/or hydrophilic polymer such as nylon, polyethylene or EVA. One suitable composition comprises 39% Pebax 63D, 39% Pebax 72D, 20% BaSO4, and 2% TiO2. Similar materials may be used for the distal section 84; however, the material of the distal section 84 can be softer than that of the proximal section 82 so that it is more easily deflected by the agitator 80. One suitable composition comprises 78% Pebax 63D, 20% BaSO4, and 2% TiO2.

Figure 4:
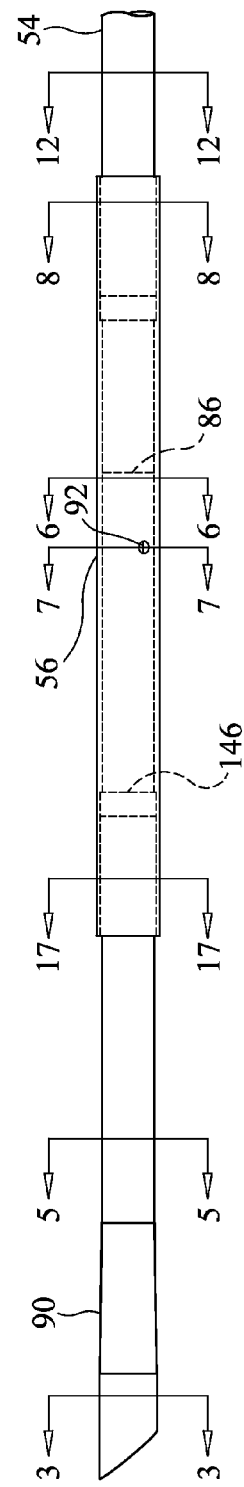
FIG. 4 is a detail view of the portion of FIG. 1 indicated by the circle 4-4.

FIG. 3 illustrates the cross-sectional configuration of the catheter 50 at the location of the line 3-3 in FIG. 4 (see area 4-4 in FIG. 1). The infusion/aspiration lumen 70 can have a circular cross-section, and occupy a majority of the cross-sectional area of the catheter 50 (e.g., 60% or more, or two-thirds or more, or about 69% in the proximal section 82 and/or 67% in the distal section 84). Each of the balloon lumens 64, 66 can have a substantially kidney-shaped cross-section, and both lumens 64, 66 can be located adjacent one another on a common side of the infusion/aspiration lumen 70. A cross-sectional area of each of the balloon lumens 64, 66 can be substantially smaller than the cross-sectional area of the infusion/aspiration lumen 70. For example, the cross-sectional area of the balloon lumen(s) can be about 0.0003 square inches in the proximal section 82 and about 0.0005 square inches in the distal section 84, while the infusion/aspiration lumen can have a cross-sectional area of about 0.0034 square inches in the proximal section 82 and about 0.0026 square inches in the distal section 84.

All three of the lumens 64, 66, 70 extend through the catheter 50 from the proximal length 52 to at least the location of the proximal balloon 56. FIG. 4 is a detail view of the portion of the catheter 50 indicated by the circle 4-4 in FIG. 1, which is within the region of the proximal balloon 56. The proximal and distal sections 82, 84 can be joined to one another at a joint 86 located beneath the proximal balloon 56. For example, the proximal and distal sections 82, 84 may be joined to one another with a butt joint 86, or any other suitable joint.

As discussed above, the proximal and distal sections 82, 84 of the catheter body 50 may have different cross-sectional configurations. However, the infusion/aspiration lumen 70 extends through the entirety of the catheter body 50, while the distal balloon inflation lumen 66 extends through portions of both the proximal and distal sections 82, 84, and the proximal balloon inflation lumen 64 extends through a portion of only the proximal section 82 (although arrangements other than the foregoing may be employed). Thus, the cross-sectional configuration of the proximal section 82 of the catheter body 50 can change toward the distal end thereof. With reference to FIG. 4, the proximal section 82 may be heated in a heating zone 88 that extends from the butt joint 86 to a location proximal of the proximal balloon 56. The heating causes the material of the catheter body 50 to melt and reflow. An outer diameter of the catheter 50 reduces slightly, creating a necked region 90 at a proximal end of the heating zone 88. During the heating process, mandrels (not shown) may be inserted through the infusion/aspiration lumen 70, the proximal balloon inflation lumen 64, and the distal balloon inflation lumen 66, so that these lumens do not completely collapse.

Figure 6:
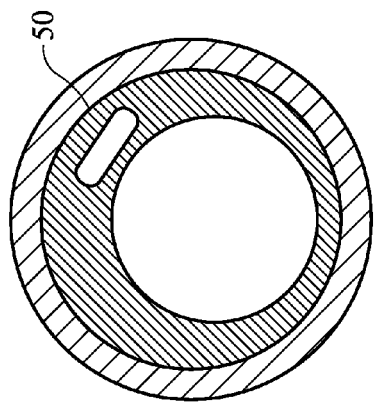
FIGS. 5-8 are cross-sectional views of the apparatus of FIG. 4 taken along the lines 5-5, 6-6, 7-7, 8-8, respectively.
Figure 5:
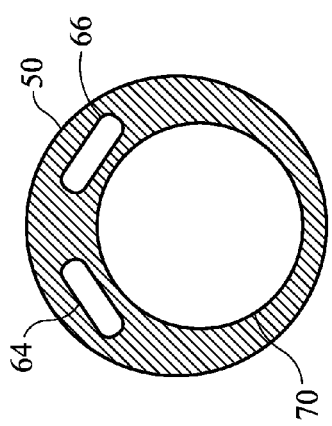

FIG. 5 illustrates the cross-sectional configuration of an embodiment of the catheter 50 at the location of the cut line 5-5 in FIG. 4, which is within the heating zone 88 just distal of the necked region 90. Comparing FIGS. 3 and 5, the diameter of the infusion/aspiration lumen 70 may be decreased in the heating zone 88. The sizes of the balloon inflation lumens 64, 66 may also be decreased, and their cross-sectional shapes may be substantially oval as opposed to the kidney shape of FIG. 3. This cross-sectional configuration of the catheter body 50 can extend toward the distal end of the proximal section 82, until just proximal of the distal end. FIG. 6 illustrates the cross-sectional configuration of the catheter 50 at the location of the cut line 6-6 in FIG. 4, which is just proximal of the distal end. The mandrel inserted into the proximal balloon inflation lumen 64 during heating may not extend through the distal end of the catheter 50, such that the proximal balloon inflation lumen 64 completely collapses distally of the mandrel. This configuration seals the proximal balloon inflation lumen 64 so that fluid injected into the proximal balloon inflation lumen 64 cannot flow past the distal end of the proximal section 82 of the catheter 50, and is instead forced into the proximal balloon 56 through a proximal balloon inflation opening 92 (FIG. 7) in the side wall of the catheter 50, as described further below. Instead of or in addition to the heating procedure described herein, other techniques (such as the use of a plug and/or adhesive) may be used to seal the distal end of the proximal balloon inflation lumen 64.

Figure 7:
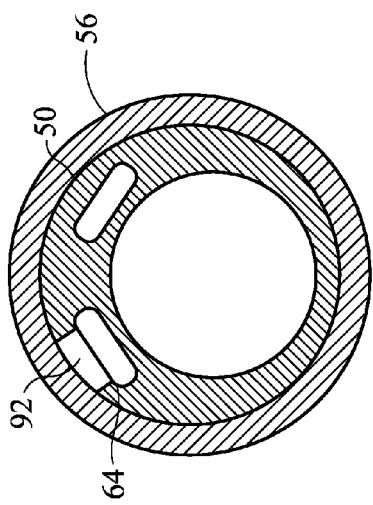

FIG. 7 illustrates an embodiment of the cross-sectional configuration of the catheter 50 at the location of the cut line 7-7 in FIG. 4, which is at the location of the proximal balloon inflation opening 92. The proximal balloon inflation opening 92 provides a fluid path from the proximal balloon inflation lumen 64 to an interior space of the proximal balloon 56. The proximal balloon 56 can thus be inflated by infusing fluid, such as saline, into the proximal balloon 56 through the proximal balloon inflation lumen 64, through the proximal balloon inflation opening 92, and into the interior space of the proximal balloon 56. The proximal balloon 56 can also be deflated by aspirating the fluid along the same path in the reverse order.

As discussed above, constructing the catheter body 50 from separate proximal and distal sections 82, 84 provides numerous advantages. For example, the proximal and distal sections 82, 84 may be constructed of different materials. A material of the proximal section 82 may have greater rigidity compared to a material of the distal section 84. Such a configuration enables the catheter body 50 to be advanced through the body by pushing from the proximal end, while maintaining flexibility along the treatment length 54 so that the treatment length 54 can more easily navigate tortuous vasculature and can accommodate an agitator shaft 110 having a larger amplitude along the treatment length 112. Example materials for the proximal and distal sections 82, 84 are discussed above.

Figure 8:
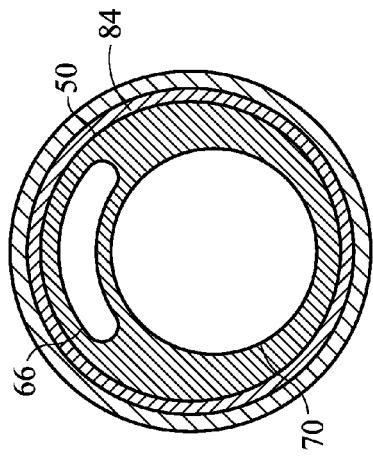

Another advantage of constructing the catheter body 50 from separate proximal and distal sections 82, 84 is that these sections can more easily be made with differing cross-sections. For example, FIG. 8 illustrates the cross-sectional configuration of the distal section 84 of the catheter 50, at the location of the cut line 8-8 in FIG. 4, which is just distal to the joint 86. The distal section 84 of the catheter 50 can include the infusion/aspiration lumen 70 and the distal balloon inflation lumen 66, but not the proximal balloon inflation lumen 64. The distal section 84, lacking the proximal balloon inflation lumen 64 that the proximal section 82 includes, can thus be made separately from the proximal section 82, and the two sections can then be secured to one another at the joint 86. Both sections can be made using standard techniques, such as extrusion, or any other process(es). Alternatively, both sections can be made as a single piece or a single extrusion, without the joint 86.

Figure 9:
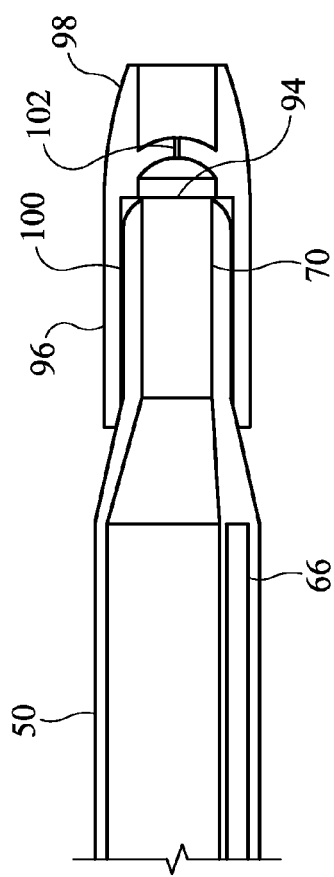
FIG. 9 is a side cross-sectional detail view of a distal end of the catheter of FIG. 1.

With continued reference to FIG. 8, the combined infusion/aspiration lumen 70 and the distal balloon inflation lumen 66 continue through the distal section 84 of the catheter 50 in the distal direction. FIG. 9 illustrates a side cross-sectional view of an embodiment of the distal end of the catheter 50. The distal balloon inflation lumen 66 terminates proximally of the distal end of the catheter 50. This configuration facilitates maintaining pressure in the distal balloon 58 when it is inflated. The combined infusion/aspiration lumen 70 extends through the distal end of the catheter 50 such that there is an opening 94 in the distal end of the catheter 50 corresponding to the lumen 70. However, a distal end cap 96 can be employed to close the distal opening 94 of the infusion/aspiration lumen 70. The distal end cap 96 is substantially cylindrical with a tapered nose portion 98. The cap 96 fits over a reduced diameter distal portion 100 of the catheter. A central portion of the cap 96 includes a narrow (relative to the infusion/aspiration lumen 70) opening 102 sized to allow a guide wire (not shown) to pass. The guide wire may be used when deploying the catheter 50 according to standard techniques. The opening 102 also provides pressure relief in the event that pressure within the infusion/aspiration lumen 70 rises. This pressure relief reduces the likelihood that fluids in the catheter 50 will flow out the proximal end, a phenomenon known as "back bleed."

Figure 10:
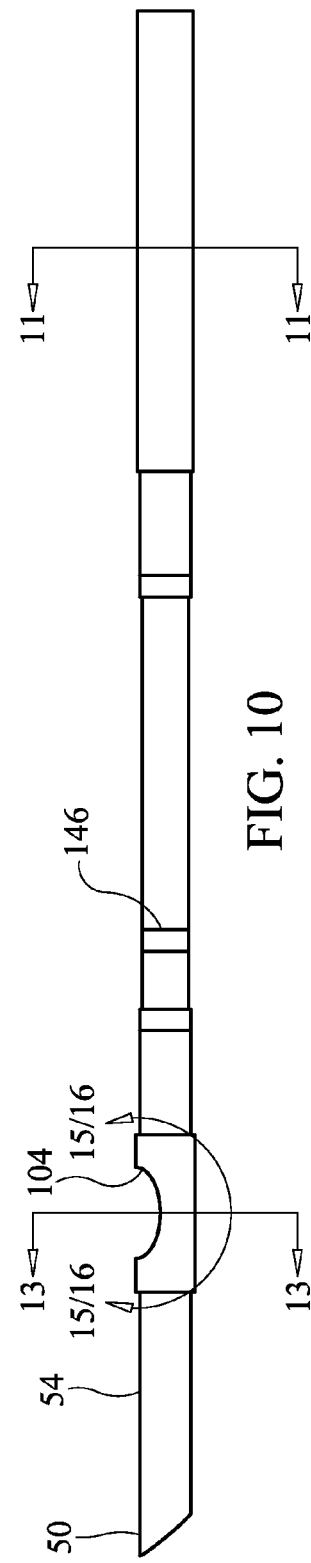
FIG. 10 is a detail view of the portion of FIG. 1 indicated by the circle 10-10.
Figure 11:
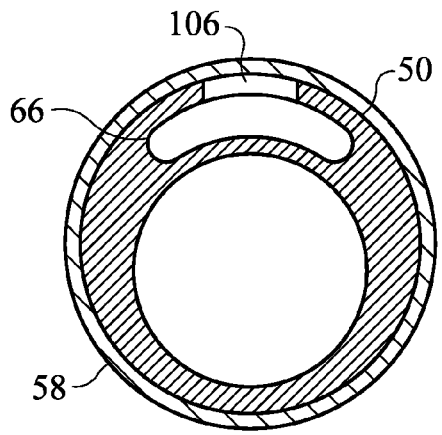
FIG. 11 is a cross-sectional view of the apparatus of FIG. 10 taken along the line 11-11.

FIG. 10 is a detail view of an embodiment of the portion of the catheter 50 indicated by the circle 10-10 in FIG. 1, which is within the region of the distal balloon 58 and the aspiration opening 104. The distal balloon 58 has been omitted from FIG. 10 for clarity. FIG. 11 illustrates the cross-sectional configuration of the catheter 50 at the location of the cut line 11-11 in FIG. 10. At the location of FIG. 11, a distal balloon inflation opening 106 in the side wall of the catheter 50 provides a fluid path from the distal balloon inflation lumen 66 to an interior space of the distal balloon 58. The distal balloon 58 can thus be inflated by infusing fluid, such as saline, into the distal balloon 58 through the distal balloon inflation lumen 66, through the distal balloon inflation opening 106, and into the interior space of the distal balloon 58. The distal balloon 58 can also be deflated by aspirating the fluid along the same path in the reverse order.

Referring back to FIG. 4, FIG. 12 illustrates an embodiment of the cross-sectional configuration of the catheter 50 at the location of the cut line 12-12, which is located between the proximal and distal balloons 56, 58. In this region, referred to as the infusion/aspiration region, the catheter 50 can include a plurality of infusion openings 108 that extend from the infusion/aspiration lumen 70 radially outward and through the side wall of the catheter 50. In the illustrated embodiment, three infusion openings 108 are provided at the location of the cut line 12-12. Additional such triads (or pairs, singles, etc.) of infusion openings 108 can be provided at axially spaced locations along the infusion/aspiration region. The axial spacing between triads may be uniform or variable.

At the location of each triad of infusion openings 108, the three openings 108 can be substantially uniformly spaced from one another at about 120° apart in the circumferential direction. The illustrated number and spacing of the infusion openings 108 is advantageous, as it provides the capability to infuse a thrombolytic agent over a radial span of substantially 360° around the outside of the catheter 50. Such "360° infusion" enables more uniform application of the thrombolytic agent to clot matter in the region of the treatment length 54 of the catheter 50 to more efficiently break down the clot. 360° infusion is facilitated at least in part by termination of the proximal balloon inflation lumen 64 proximally of the locations of the infusion openings 108. Reducing the total number of lumens in the catheter 50 in the infusion/aspiration region leaves a larger radial portion of the catheter 50 through which the infusion openings 108 can extend from the infusion/aspiration lumen 70 without interfering with other lumens.

As described in further detail below, thrombolytic agent may be infused at a treatment site within a vessel by injecting the lytic at the infusion/aspiration port 68 (FIG. 1), where it flows into and through the infusion/aspiration lumen 70 and eventually out the infusion openings 108. Because the infusion openings 108 are distributed along the axial length of the catheter body 50, it is advantageous for a diameter of each infusion opening 108 to be small compared to a diameter of the infusion/aspiration lumen 70. Such a configuration facilitates maintaining a substantially uniform infusion pressure at each infusion opening 108, as opposed to more proximal infusion openings 108 having higher infusion pressures than more distal infusion openings 108. For example, in certain of the present embodiments a diameter of the infusion/aspiration lumen 70 may be in the range 0.065-0.067 inches in the proximal section 82 and 0.057-0.059 inches in the distal section 84, while a diameter of each infusion opening 108 may be in the range 0.0025-0.0055 inches.

In certain embodiments, locations of at least some of the triads (or pairs, singles, groups of four, etc.) of infusion openings 108 may be located at peaks 150 of the treatment length 112 of the agitator shaft 110 (FIG. 2). Such a configuration locates the infusion openings 108 as close as possible to the wall of the vessel at the treatment site for more effective chemical breakdown of the clot.

With reference to FIG. 10, the sidewall of the catheter body 50 can further include an aspiration opening 104 located in the infusion/aspiration region. In the illustrated embodiment, the aspiration opening 104 is just proximal of the distal balloon 58. That is, the aspiration opening 104 is closer to the distal balloon 58 than it is to the proximal balloon 56. This configuration provides advantages. For example, during a treatment procedure where the treatment site is accessed from an upstream location (antegrade), an operator may deflate the proximal balloon 56 prior to aspirating dissolved clot, and any solid clot that may be present, from the treatment site. Blood will thus flow toward the treatment site and push any fragmented matter toward the aspiration opening 104, making it more likely that all of the fragmented matter will be aspirated out of the vasculature. Processes for using the present embodiments are described in further detail below.

Figure 13:
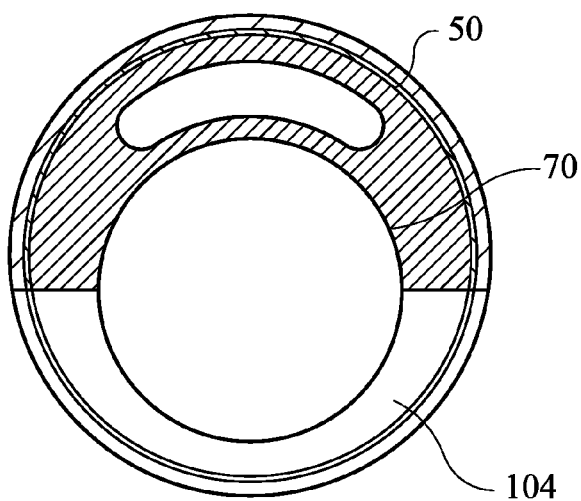
FIG. 13 is a cross-sectional view of the apparatus of FIG. 10 taken along the line 13-13.

FIG. 13 illustrates the cross-sectional configuration of the catheter 50 at the location of the cut line 13-13 in FIG. 10, which is located at the aspiration opening 104. Note that the scale of FIG. 13 is larger than that of the other cross-sectional views to more clearly illustrate the various layers of the apparatus. With reference to FIG. 13, the aspiration opening 104 provides fluid communication between the infusion/aspiration lumen 70 and the vascular space surrounding the catheter body 50. Further, a size of the aspiration opening 104 is preferably adequate to allow the passage of dissolved clot, as well as solid pieces of clot that have been fragmented from the solid clot matter in the vessel at the treatment site. These dislodged pieces can thus be drawn into the infusion/aspiration lumen 70 through the aspiration opening 104 and evacuated from the vessel, as described in detail below. For example, the aspiration opening 104 may have a length of about 0.22 inches and a width of about 0.08 inches, although other sizes or configurations may be employed.

Certain disclosed embodiments advantageously enable infusion of thrombolytic agent and aspiration of dissolved clot, and any solid clot that may be present, to be performed through the same lumen (the infusion/aspiration lumen 70) in the catheter 50. Infusion and aspiration can be achieved with the aid of the agitator 80 (FIG. 2), which can be slidably received within the infusion/aspiration lumen 70, as described below. With reference to FIG. 2, the agitator 80 includes an elongate shaft 110 that is generally straight over its entire length, except along a treatment length 112 thereof, which includes a non-linear curvature. (The agitator shaft 110 is shown in FIG. 2 as having a 180° bend merely for illustration purposes. In an at-rest state, the agitator shaft 110 is generally straight except along the treatment length 112.) In the illustrated embodiment, the curvature of the treatment length 112 is sinusoidal, but other forms of curvature could be provided instead.

The preferred agitator shaft 110 is generally flexible, but includes sufficient rigidity that it may be pushed distally through the infusion/aspiration lumen 70 by force applied at the proximal end of the agitator 80. Example materials for the agitator shaft 110 include metals, such as stainless steel or any other metal displaying good fatigue properties, and polymers, such as polytetrafluoroethylene (PTFE), polyether ether ketone (PEEK), or thermoplastic polyetherimide (ULTEM™), or any other stiff thermoplastic polymer with good fatigue properties. The agitator shaft 110 is further sized to be slidably received within the infusion/aspiration lumen 70. An outside diameter of the agitator shaft 110 may be in the range 0.0385-0.0425 inches, or about 0.0410 inches. The agitator 80 may include a lubricious coating, such as a PTFE or FEP coating which may be applied via heat-shrink or dip coating.

In one embodiment, the shaft 110 includes a stainless steel core with an outer shell or coating of PTFE and PEEK. The PEEK is located along the treatment length 112 only, while the PTFE covers substantially all portions of the shaft 110 and is positioned over the PEEK. Providing PEEK along the treatment length 112 facilitates forming the sinusoidal curvature, because the PEEK can be heat set to permanently assume the curved shape.

With reference to FIG. 2, the agitator shaft 110 extends distally from an oscillation drive unit (ODU) 114. The ODU 114 comprises a housing 116 that can enclose a powered drive unit (not shown). The powered drive unit may comprise, for example, an electric motor, or any other apparatus capable of rotating the agitator shaft 110. The powered drive unit may be connected to a power source (not shown), such as a battery, which may also be enclosed in the housing 116. An on/off switch 118 on the housing 116 may be activated to start and stop rotation/oscillation of the agitator shaft 110. The on/off switch 118 may include an indicator light 120, such as a light-emitting diode (LED), that provides a visual indication when the powered drive unit is activated and the agitator shaft 110 is rotating/oscillating. Opposite sides of the housing 116 may include raised ridges 122, or other tactile features, to facilitate gripping of the ODU 114. Preferably, the ODU 114 is sized to be comfortably gripped with one hand. A distal edge 124 of the housing 116 includes a connector 126 that is configured to mate with the connector 78 at the proximal end of the catheter 50 (FIG. 1). For example, the connector 126 may comprise a male Luer-type connector, such as a LUER-LOK® connector, for sealing engagement with a female LUER-LOK® connector at the proximal end of the catheter 50.

In certain embodiments, a speed of rotation of the agitator shaft 110 may be adjustable. Thus, with continued reference to FIG. 2, the ODU 114 further includes a speed control 128. In the illustrated embodiment, the speed control 128 is a rotatable knob, but in other embodiments could comprise other configurations, such as a sliding member. When the agitator shaft 110 is activated to rotate, adjustment of the speed control 128 adjusts a speed of rotation of the agitator shaft 110. The speed of rotation of the agitator shaft 110 may be adjustable between, for example, 500 RPM (e.g. 400-600 RPM) and 3000 RPM (e.g. 2550-3450 RPM).

Also in certain embodiments, an axial position of the agitator shaft 110 relative to the ODU 114 may be adjustable. Thus, with continued reference to FIG. 2, the ODU 114 further includes a translation bar 130. The translation bar 130 is operatively connected to the agitator shaft 110, such that translating the translation bar 130 along the ODU 114 moves the agitator shaft 110 away from and toward the ODU 114. The operator may move the translation bar 130 by, for example, cradling the ODU 114 with one hand and sliding the translation bar 130 backward and forward with the thumb of the same hand. In certain embodiments, the ODU 114 and the translation bar 130 may include detents (not shown) such that the agitator shaft 110 is translatable between or among discrete positions, such as three discrete positions, located along the longitudinal range of motion of the agitator shaft 110. In other embodiments, the agitator shaft 110 may be continuously translatable, in other words without discrete positions.

Figure 2A:
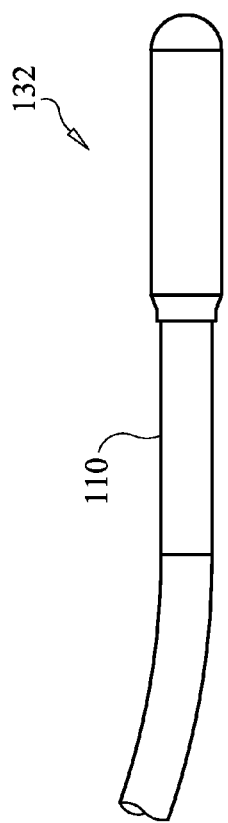
FIG. 2A is a detail view of the portion of FIG. 2 indicated by the circle 2A-2A.

FIG. 2A illustrates a detail view of the distal end portion of an embodiment of the agitator shaft 110, as indicated by the circle 2A-2A in FIG. 2. An outside diameter of the agitator shaft 110 can be substantially constant over its length, except at the distal end portion, which can include an expanded diameter distal tip portion or valve body 132. As described below, the distal tip portion 132 is sized to substantially correspond to an internal diameter of the infusion/aspiration lumen 70, with a slight clearance, so that the agitator 80 may be slid longitudinally within the infusion/aspiration lumen 70 without substantial difficulty.

Figure 14:
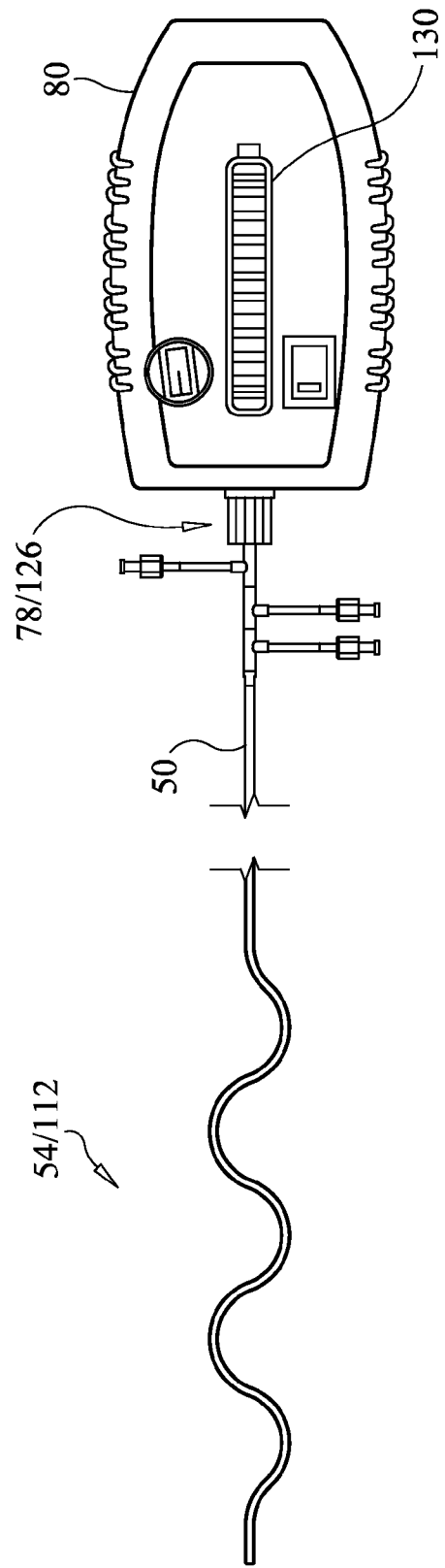
FIG. 14 is a top plan view of the catheter of FIG. 1 coupled with the agitator of FIG. 2.

FIG. 14 illustrates the agitator 80 engaged with the catheter body 50. The connectors 78, 126 on the catheter 50 and the ODU 114 are sealingly engaged to secure the agitator 80 to the catheter body 50. The agitator shaft 110 is received within the infusion/aspiration lumen 70, and the treatment length 54 of the catheter 50 assumes the sinusoidal shape of the treatment length 112 of the agitator shaft 110. When the agitator 80 is engaged with the catheter body 50, movement of the translation bar 130 longitudinally translates the agitator shaft 110 within the infusion/aspiration lumen 70, as described further below.

Figure 15:
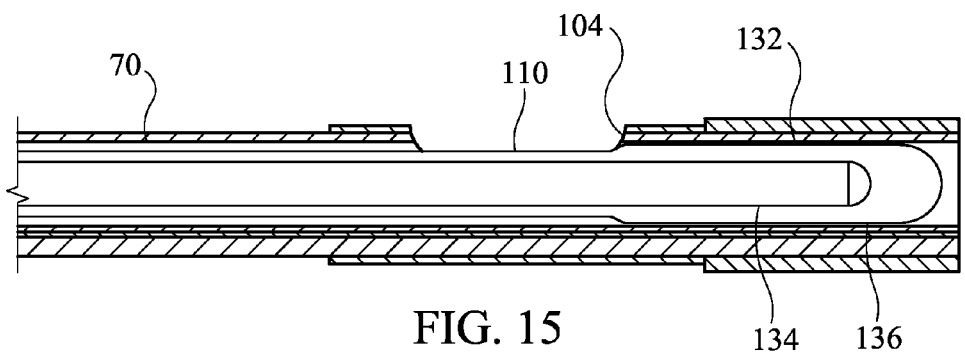
FIGS. 15 and 16 are side cross-sectional detail views of the portion of FIG. 10 indicated by the circle 15/16-15/16.
Figure 16:
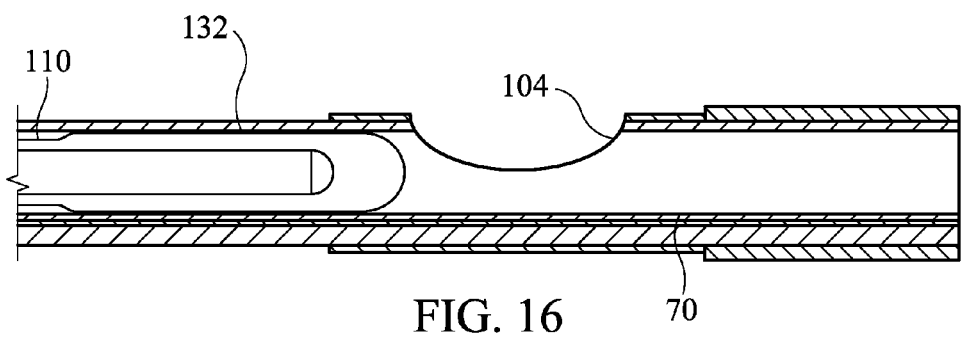

FIGS. 15 and 16 illustrate side cross-sectional views of the treatment length 54 of the catheter 50 in the region of the aspiration port, as indicated by the circle 15/16-15/16 in FIG. 10. With reference to FIG. 15, the agitator shaft 110 is disposed within the infusion/aspiration lumen 70. The distal tip portion 132 substantially blocks fluid flow through the infusion/aspiration lumen 70. Depending upon whether the distal tip portion 132 is positioned proximally or distally of the aspiration opening 104, either of infusion or aspiration may be performed through the lumen 70, as described below. As discussed above, the agitator shaft 110 is linearly translatable within the infusion/aspiration lumen 70 under the influence of the translation bar 130. Thus, to switch between infusion and aspiration, the operator may translate the translation bar 130 proximally and distally to adjust the relative positions of the distal tip portion 132 and the aspiration opening 104, as described below.

For example, FIG. 16 illustrates the agitator shaft 110 with the distal tip portion 132 positioned proximally of the aspiration opening 104. In this position, fluid communication between the infusion/aspiration port 68 (FIG. 1) and the aspiration opening 104 is substantially blocked. Thus, if fluid is infused through the infusion/aspiration port 68 it flows through the infusion/aspiration lumen 70 before being forced out of the infusion openings 108 (FIG. 12) proximal of the distal tip portion 132 (which itself is proximal of the aspiration opening 104). This position of the distal tip portion 132 may thus be referred to as the infusion position, and may correspond to a second, or middle position of the translation bar 130 with respect to the ODU 114.

By contrast, FIG. 15 illustrates the agitator shaft 110 with the distal tip portion 132 positioned distally of the aspiration opening 104. In this position, fluid communication between the infusion/aspiration port 68 (FIG. 1) and the aspiration opening 104 is open. Thus, if suction is applied at the infusion/aspiration port 68, it creates suction in the infusion/aspiration lumen 70, which in turn creates suction at the aspiration opening 104. Disrupted pieces of clot and/or fluid can thus be evacuated from the treatment site through the aspiration opening 104 and the infusion/aspiration lumen 70. This position of the distal tip portion 132 may thus be referred to as the aspiration position. Further, because the interaction of the distal tip portion 132 and the aspiration opening 104 can switch the apparatus between an infusion state and an aspiration state, at least the distal tip portion 132 and the aspiration opening 104 may be referred to collectively as a valve, or an infusion/aspiration valve. The aspiration position of the distal tip portion 132 may correspond to a third, or distal most position of the translation bar 130 with respect to the ODU 114.

With further reference to FIG. 15, and as discussed above, the agitator shaft 110 in certain embodiments may include an inner core 134 and an outer sleeve 136. The inner core 134 and outer sleeve 136 may be constructed of different materials. For example, the inner core 134 may be constructed of a metal, such as stainless steel, and the outer sleeve 136 may be constructed of a polymer, such as polytetrafluoroethylene (PTFE) and/or polyether ether ketone (PEEK).

With reference back to FIG. 4, the proximal balloon 56 can be located around and secured to an outer surface of the catheter 50 at a proximal end of the treatment length 54 thereof. Similarly, with reference to FIG. 10, the distal balloon 58 can be located around and secured to an outer surface of the catheter 50 at a distal end of the treatment length 54 thereof. The distal balloon 58 has been omitted from FIG. 10 for clarity. The balloons 56, 58 can be secured to the catheter 50 at either end, with an intermediate portion of each balloon 56, 58 being unsecured to the catheter 50, so that upon inflation the balloons 56, 58 assume a spheroid shape or other similar shape suitable for occluding a vessel. The shape of the inflated balloons 56, 58 should not be interpreted as limiting. Any expanded shape suitable for occluding a vessel, such as a torus or any other shape, is within the scope of the present disclosure.

The balloons 56, 58 may be constructed of one or more materials that are preferably durable and elastic. For example, the balloons 56, 58 may be constructed of a thermoplastic elastomer, such as ChronoPrene™, or other compliant polymers such as ChronoFLEX™, Polyblend™, or Chronosil™.

In certain embodiments, the opposite ends of each balloon 56, 58 may be bonded to the catheter 50. For example, each balloon 56, 58 may be heat bonded to the catheter 50. However, in certain embodiments the balloons 56, 58 may be constructed of ChronoPrene™, and the catheter distal section 84 may be constructed of a polyether block amide. ChronoPrene and polyether block amide do not heat bond well to one another, and are subject to delamination. The present embodiments solve this incompatibility problem by introducing a tie layer 138 between each balloon and the catheter 50.

Figure 17:
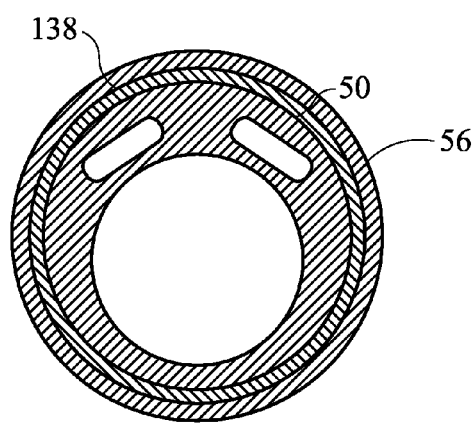
FIG. 17 is a cross-sectional view of the apparatus of FIG. 4 taken along the line 17-17.

FIG. 17 illustrates the cross-sectional configuration of one embodiment of the catheter 50 at the location of the cut line 17-17 in FIG. 4, which is located in the proximal bond region of the proximal balloon 56. With reference to FIG. 17, the tie layer 138 can be interposed between each balloon 56, 58 and the catheter 50, and act as a link between the two. The tie layer 138 comprises a material that bonds well with both the material of the balloons 56, 58 and the material of the catheter 50. In embodiments in which the balloons 56, 58 are ChronoPrene™ and the catheter distal section 84 is a polyether block amide, the tie layer 138 may comprise a compound of a polyolefin elastomer and polyether block amide, or a compound of a polyolefin elastomer and urethane. In certain embodiments, the ratio of polyolefin elastomer to polyether block amide or urethane may be 60/40. Also in certain embodiments, the polyolefin elastomer may be the type sold under the trademark ENGAGE®, available from Dow Chemical, and the polyether block amide may be the type sold under the trademark PEBAX®, available from Arkema. In alternative embodiments, the tie layer 138 may itself comprise more than one layer. For example, the tie layer 138 may comprise two layers, with an inner layer of polyether block amide and an outer layer of polyolefin elastomer.

Where employed, the tie layer 138 provides advantages. For example, one prior art method of securing balloons to catheters involves wrapping thread around the ends of each balloon. The thread increases the overall diameter and stiffness of the device as compared to devices that don't include thread. The tie layer 138 thus enables the insertion profile of the catheter 50 to be reduced, enabling it to be used in narrower spaces. The tie layer 138 also provides greater directional specificity, reducing the likelihood of lopsided balloons adjacent to the points where they are bonded to the catheter as compared to thread-wrapped balloons.

Method of Use

FIGS. 18-25 illustrate one embodiment of a method of use of the present apparatus and methods for clot disruption and evacuation. The operator may begin by preparing the apparatus, for example performing such steps as flushing the infusion/aspiration lumen 70 with saline, filling two balloon inflation syringes with saline and connecting them to the proximal and distal balloon inflation ports 60, 62, and/or filling a syringe with a thrombolytic solution and connecting it to the infusion/aspiration port 68. Then, using standard techniques the operator may gain vascular access at an access site (e.g. the popliteal vein behind the knee, the femoral vein at the groin, or in the brachial vein in the arm) remote from a treatment site, and advance the catheter 50 toward the treatment site (e.g., the inferior vena cava, or any of the following veins: isolated iliac, iliofemoral, isolated popliteal, isolated femoral, subclavian, or any other suitable vein or artery).

Figure 18:
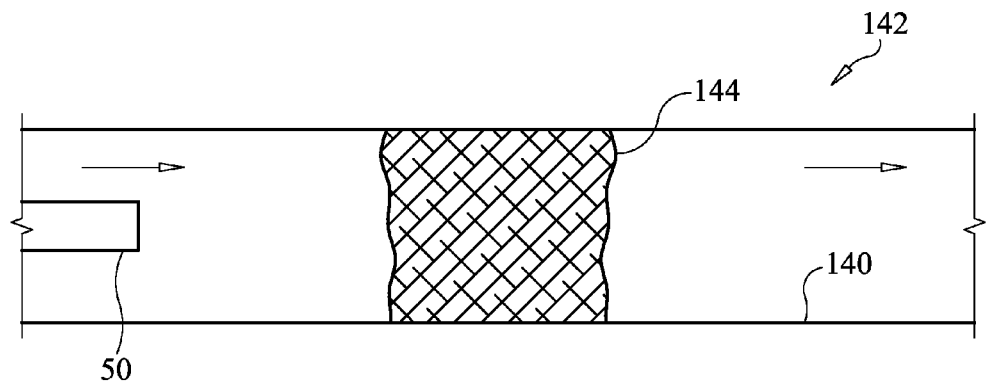
FIGS. 18-25 are side elevation views of a method for clot disruption and evacuation according to one of the present embodiments.

With reference to FIG. 18, the vessel 140 is occluded at the treatment site 142 by a clot 144 or thrombus. In various embodiments, the vessel 140 may be completely occluded, or only partially occluded. As discussed further below, it is advantageous for the catheter 50 to be advanced toward the treatment site 142 in the downstream direction, as indicated by the arrows showing the direction of blood flow. However, the present embodiments are not limited to this direction of approach.

Figure 19:
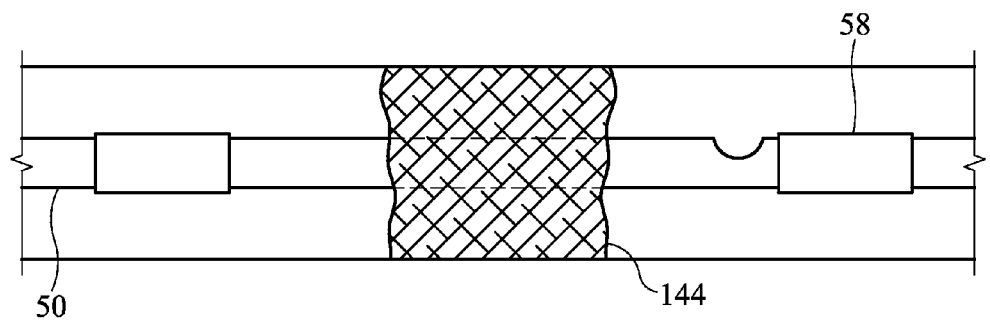

With reference to FIG. 19, the catheter 50 is advanced through the clot 144 until the distal balloon 58 is entirely distal of the clot 144. Advancement of the catheter 50 may be aided by a guide wire and/or an introducer sheath using standard techniques. However, for clarity those components have been omitted from the figures. If a guide wire is used, the catheter 50 may be advanced over the guide wire with the guide wire passing through the infusion/aspiration lumen 70 and the opening 102 (FIG. 9).

With reference back to FIGS. 4 and 10, the catheter 50 may include one or more marker bands 146 to aid in external visualization of the position of the treatment length 54 of the catheter 50. In the illustrated embodiment, the catheter 50 includes a pair of radiopaque bands 146 positioned beneath each of the balloons 56, 58. Using fluoroscopy, the operator may accurately position the treatment length 54 of the catheter 50 at the treatment site 142 using the radiopaque bands 146 as a guide. Other external visualization techniques, such as ultrasound, may be used instead of fluoroscopy, which is recited here merely as one example technique.

Figure 20:
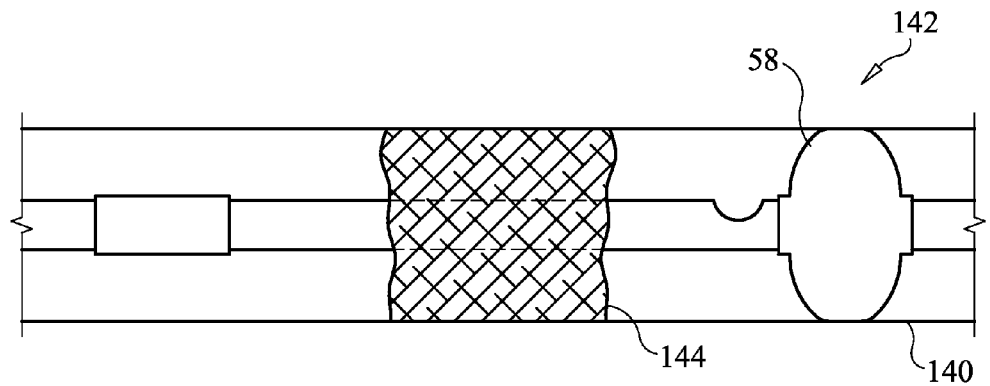

With reference to FIG. 20, the distal balloon 58 is inflated by depressing the plunger on the syringe connected to the distal balloon inflation port 62. The distal balloon 58 is inflated until it completely occludes the vessel 140 distal of the clot 144. Complete occlusion is advantageous to prevent fragmented pieces of the clot 144 from flowing downstream away from the treatment site 142.

Figure 21:
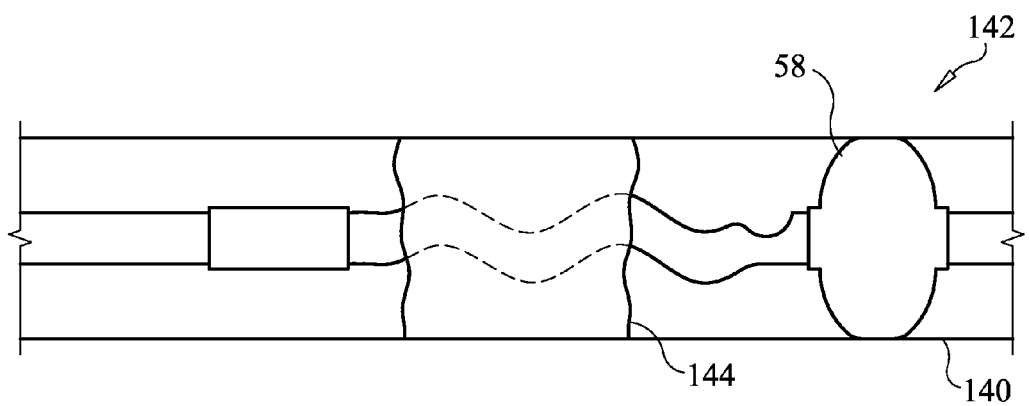

With reference to FIG. 21, the agitator 80 is advanced through the infusion/aspiration lumen 70 of the catheter 50 until the sinusoidally curved treatment length 112 of the agitator 80 is positioned between the balloons. At this point, the operator connects the connectors on the proximal end of the catheter 50 and the distal edge of the ODU 114 housing 116 to secure the agitator 80 to the catheter 50. The operator may ensure that the translation bar 130 is in the first or second position, which correspond to infusion positions. Alternatively, the operator may postpone this step until later in the procedure.

Figure 22:
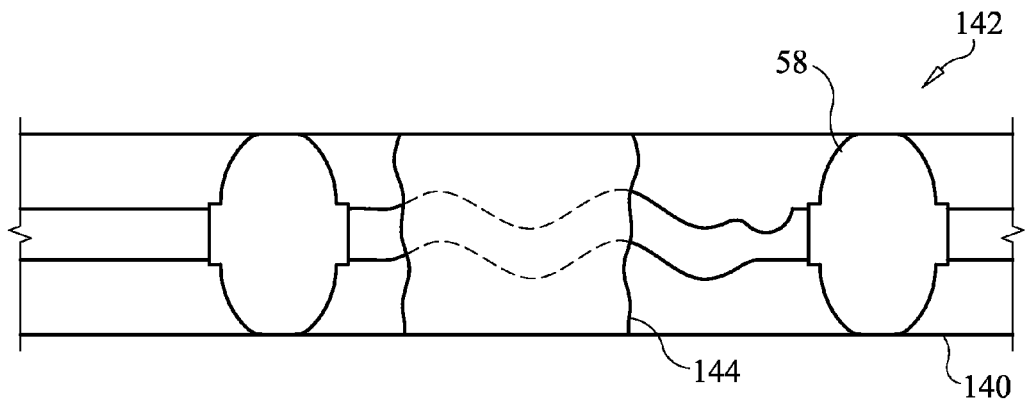

With reference to FIG. 22, the proximal balloon 56 is inflated by depressing the plunger on the syringe connected to the proximal balloon inflation port 60. Again, the proximal balloon 56 is inflated until it completely occludes the vessel 140 proximal of the clot 144. At this point, the clot 144 is isolated between the inflated balloons.

With the translation bar 130 in the first or second position, the operator next activates the ODU 114 to begin rotation/oscillation of the agitator 80. The operator may adjust the rotational speed of the agitator 80 using the speed control 128 (FIG. 2) until a desired rotational speed is achieved. The treatment length 112 of the agitator 80, with its sinusoidal curvature, acts to mechanically disrupt the clot 144 along the treatment length and/or to disperse lytic at the treatment site to facilitate dissolving of the clot. The dimensions of the treatment length 112 are such that it contacts the clot 144 when it rotates, disrupting and tearing away fragments thereof as it rotates.

Figure 12:
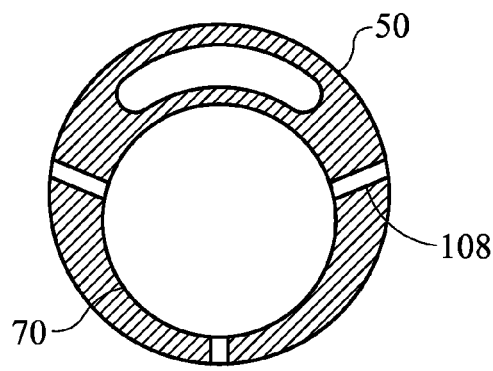
FIG. 12 is a cross-sectional view of the apparatus of FIG. 4 taken along the line 12-12.

While the agitator 80 rotates at the desired speed, the operator infuses a quantity of thrombolytic solution by depressing the plunger on the syringe connected to the infusion/aspiration port 68. The lytic travels through the infusion/aspiration lumen 70 and is distributed at the treatment site 142 through the infusion openings 108 in the catheter 50 (FIG. 12). The lytic acts to chemically break down the clot 144 so that it may be more easily disrupted by the rotating agitator 80. The operator may periodically infuse additional discrete quantities of thrombolytic solution as the procedure progresses. For example, the operator may infuse additional lytic every thirty seconds, or every sixty seconds, or every ninety seconds, etc., until all of the lytic in the infusion/aspiration syringe has been infused. The operator may infuse the same quantity of lytic each time, or may vary the infused quantity from one infusion to another. For example, the operator may inject a first quantity and a last quantity having the same volume, with one or more intermediate quantities having half of the volume of lytic as the first and last quantities. For example, during a ten minute run time, the operator may follow an infusion schedule under which the operator infuses 2 cc of lytic at the beginning of the run, and an additional 1 cc of lytic at the end of each of the first through ninth minutes of the run.

Periodically while the agitator 80 is rotating the operator may adjust the longitudinal position of the treatment length 112 of the agitator 80. As described above, the translation bar 130 may include three discrete positions. Two of these positions have been described above with respect to FIGS. 15 and 16. A third position, or proximal most position, may also correspond to an infusion position, in which the expanded diameter distal tip portion or valve body 132 of the agitator 80 is located proximally of the aspiration opening 104 in the sidewall of the catheter body 50. By alternating the agitator treatment length 112 between the two infusion positions, the clot 144 can be more effectively disrupted, because the sinusoidal curvature of the treatment length 112 is brought to bear against a greater proportion of the length of the clot 144, and because the lytic is better dispersed. The operator may, for example, adjust the position of the agitator 80 each time he or she infuses lytic.

Figure 23:
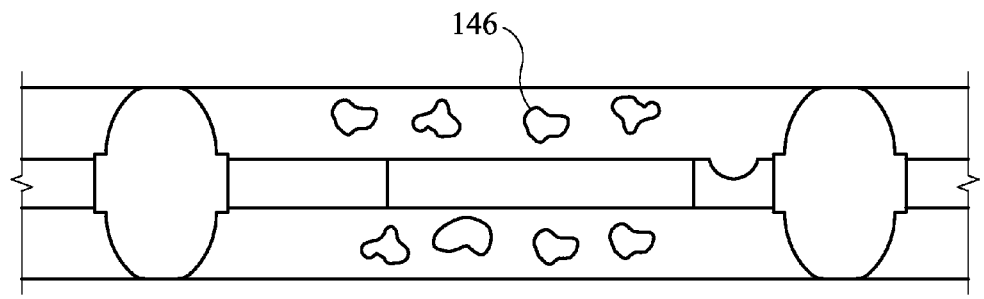

After the operator has infused the last quantity of lytic, the procedure may continue with the agitator 80 rotating for a desired amount of time, such as 5-15 minutes. At this time, the operator may verify the effectiveness of clot 144 disruption using any desired imaging technique, such as ultrasound, fluoroscopy, etc. If the results are not satisfactory, the steps described above may be repeated. However, if the results are satisfactory, the operator may begin aspirating dissolved clot, and any fragmented pieces 146 of clot 144 that may be present, from the treatment site 142. FIG. 23 illustrates the treatment site 142 after clot 144 disruption, with fragmented pieces 146 of the clot 144. The agitator 80 is not shown in FIG. 23 for clarity.

Figure 24:
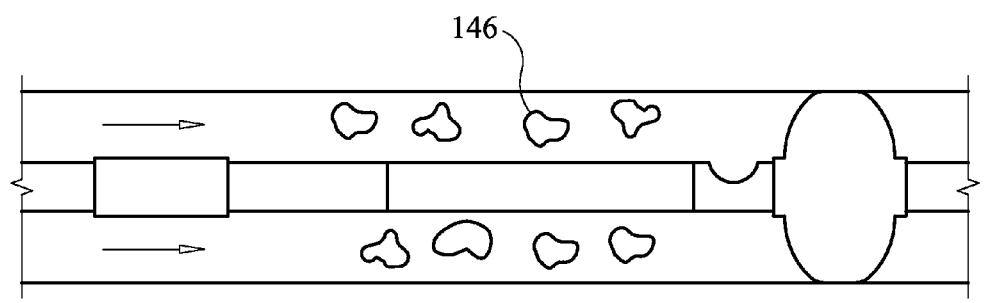
Figure 25:
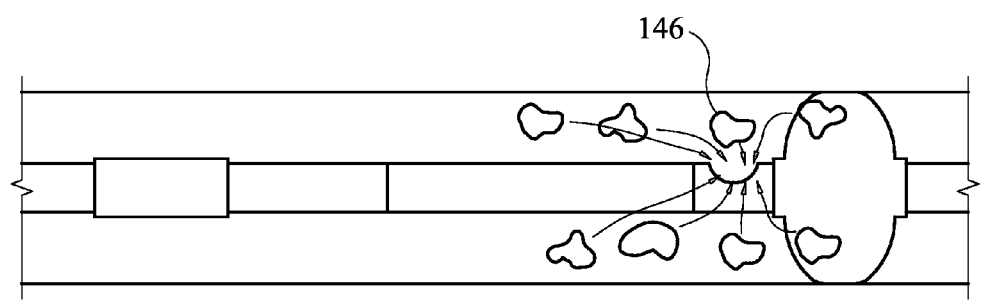

To aspirate, the operator may first reduce the rotational speed of the agitator 80. With reference to FIG. 24, the proximal balloon 56 may then be deflated if the procedure is being performed antegrade (i.e. blood flow at the treatment site 142 is in the proximal-to-distal direction with reference to the catheter 50). If the procedure is being performed retrograde, the distal balloon 58 is deflated while the proximal balloon 56 remains inflated (not shown). The advantage of deflating the proximal balloon 56 for antegrade procedures and deflating the distal balloon 58 for retrogrades is that blood flow entering the treatment area pushes the disrupted clot 144 particles downstream where they are trapped by the still inflated downstream balloon. When performed antegrade, this direction of flow has the additional advantage of pushing the fragmented clot pieces 146 toward the aspiration opening 104 in the catheter 50, which is located closer to the distal balloon 58 than the proximal balloon 56.

The operator next moves the translation bar 130, and hence the agitator 80, to the aspiration position in which the expanded diameter distal tip portion 132 of the agitator 80 is located distally of the aspiration opening 104 in the sidewall of the catheter body 50, as shown in FIG. 15. The operator then aspirates the dissolved clot, and any fragmented clot pieces 146 that may be present, from the treatment site 142 by drawing back on the plunger of the infusion/aspiration syringe. In certain embodiments, the operator may exchange an infusion syringe for a separate and larger aspiration syringe prior to beginning aspiration. The dissolved clot, fragmented clot pieces 146, along with remnants of any infused fluids and/or blood, are aspirated through the aspiration opening 104 (FIG. 25), and flow proximally through the infusion/aspiration lumen 70 and into the infusion/aspiration syringe. The operator may need to perform this step more than once to ensure that all fragmented clot pieces 146 are aspirated.

When aspiration is complete, the operator halts rotation of the agitator 80, and removes the agitator 80 from the catheter 50. The operator may then optionally reinsert a guide wire through the infusion/aspiration lumen 70. The operator then deflates the second balloon and withdraws the catheter 50.

The embodiments described herein may provide numerous advantages. For example, the catheter 50 can include only three lumens in its proximal section 82, and/or only two lumens in its distal section 84. Reducing the number of lumens enables the infusion/aspiration lumen 70 to be made larger. A larger infusion/aspiration lumen 70 enables larger fragmented clot pieces 146 to pass, making it less likely that the infusion/aspiration lumen 70 will get clogged. Reducing the number of lumens also enables "360° infusion," which is discussed above.

One reason the present embodiments are capable of functioning with so few lumens in the catheter 50 is because infusion and aspiration are performed through the same lumen. There is thus no need for two separate lumens for infusion and aspiration. This functionality is at least partially enabled by the infusion/aspiration valve, which is discussed above.

The above description presents the best mode contemplated for carrying out the present apparatus and methods for clot disruption and evacuation, and of the manner and process of making and using them, in such full, clear, concise, and exact terms as to enable any person skilled in the art to which they pertain to make and use the present embodiments. The present embodiments are, however, susceptible to modifications and alternate constructions from that discussed above that are fully equivalent. Consequently, the present apparatus and methods are not limited to the particular embodiments disclosed. On the contrary, the present embodiments cover all modifications and alternate constructions coming within the spirit and scope of the present embodiments as generally expressed by the following claims, which particularly point out and distinctly claim the subject matter of the present embodiments.

What is claimed is:

1. Apparatus for disrupting a clot in a blood vessel, the apparatus comprising:
   a catheter body having a proximal length and a treatment length;
   at least one port along the proximal length of the catheter body;
   at least one infusion opening along the treatment length of the catheter body;
   at least one aspiration opening along the treatment length of the catheter body;
   a first lumen within the catheter body in fluid communication with the at least one infusion opening and in fluid communication with the at least one aspiration opening;
   a valve member along the treatment length of the catheter body, the valve member being configured to selectively open and close fluid communication between the port and the at least one aspiration opening, wherein the valve member comprises a body that is translatable longitudinally within the first lumen, and wherein the body of the valve member comprises a first position located proximally of the at least one aspiration opening; and
   an agitator that is translatable longitudinally within the first lumen, wherein the agitator comprises an elongate member having a non-linear portion, and wherein the body of the valve member is located at a distal portion of the agitator.

2. The apparatus of claim 1, wherein when the body of the valve member is in the first position the apparatus is configured to infuse a thrombolytic agent into the vessel through the first lumen and the at least one infusion opening, and when the body of the valve member is in the second position the apparatus is configured to aspirate the dissolved clot, and any pieces of solid clot that may be present, from the vessel through the at least one aspiration opening and the first lumen.

3. The apparatus of claim 1, further comprising an aspiration source; wherein when the body of the valve member is in the first position the body substantially blocks fluid communication within the first lumen between the at least one aspiration opening and the aspiration source, and when the body of the valve member is in the second position the body does not block fluid communication within the first lumen between the at least one aspiration opening and the aspiration source.

4. The apparatus of claim 3, further comprising an infusion source; wherein when the body of the valve member is in the first position the body substantially blocks fluid communication within the first lumen between the at least one aspiration opening and the at least one infusion source, the body of the valve member therefore being configured to cause fluid flowing from the infusion source to flow out of the first lumen through the at least one infusion opening.

5. The apparatus of claim 1, further comprising a first expandable member along the treatment length of the catheter body, the first expandable member defining a first expandable internal volume.

6. The apparatus of claim 5, further comprising a second lumen within the catheter body in fluid communication with the first expandable internal volume of the first expandable member.

7. The apparatus of claim 6, further comprising a second expandable member along the treatment length of the catheter body, the second expandable member defining a second expandable internal volume.

8. The apparatus of claim 7, further comprising a third lumen within the catheter body in fluid communication with the second expandable internal volume of the second expandable member.

9. The apparatus of claim 8, wherein the second lumen terminates at the first expandable internal volume of the first expandable member and the third lumen terminates at the second expandable internal volume of the second expandable member.

10. The apparatus of claim 7, wherein the at least one infusion opening and the at least one aspiration opening are located between the first and second expandable members.

11. The apparatus of claim 10, wherein the at least one infusion opening comprises a plurality of infusion openings that are spaced radially around the catheter body, over a radial span of greater than 180° about the longitudinal axis of the catheter body.

12. The apparatus of claim 11, wherein the infusion openings are located on a portion of the catheter body that comprises no lumens other than the first lumen and the second lumen, the first lumen and the second lumen being collectively sufficient to facilitate infusion through the infusion openings, aspiration through the at least one aspiration opening, and expansion of one of the expandable members.

13. The apparatus of claim 5, wherein the catheter body comprises a proximal portion and a distal portion secured to one another at a joint, and the first expandable member surrounds the joint.

14. The apparatus of claim 13, wherein the joint is a butt joint.

15. The apparatus of claim 1, wherein the at least one infusion opening comprises a plurality of infusion openings, and the infusion openings are spaced from one another both radially and longitudinally with respect to the treatment length of the catheter body.

16. The apparatus of claim 15, wherein the infusion openings are grouped in groups of three, with each group of three infusion openings being located at a same position along the treatment length of the catheter body.

17. The apparatus of claim 16, wherein the infusion openings in each group of three infusion openings are uniformly radially spaced 120° from one another.

18. The apparatus of claim 1, wherein the agitator is configured to mechanically disrupt the clot and/or to disperse lytic to facilitate dissolving the clot.

19. The apparatus of claim 1, wherein the first position of the body of the valve member closes fluid communication between the port and the aspiration opening, and wherein the second position of the body of the valve member opens fluid communication between the port and the aspiration opening.

20. The apparatus of claim 1, wherein a first diameter of the body of the valve member is larger than a second diameter of a proximal portion of the agitator.

* * * * *